(12) United States Patent
Lescuyer et al.

(10) Patent No.: US 7,767,401 B2
(45) Date of Patent: Aug. 3, 2010

(54) DIAGNOSTIC METHOD FOR STROKE

(75) Inventors: Pierre Lescuyer, Annemasse (FR); Denis Francois Hochstrasser, Geneva (CH); Jean-Charles Sanchez, Bernex (CH); Laure Allard, Gaillard (FR); Elisabeth Guillaume, Divonne les Bains (FR)

(73) Assignee: Electrophoretics Limited, Cobham, Surrey (GB)

( * ) Notice: Subject to any disclaimer, the term of this patent is extended or adjusted under 35 U.S.C. 154(b) by 822 days.

(21) Appl. No.: 10/568,093

(22) PCT Filed: Aug. 16, 2004

(86) PCT No.: PCT/GB2004/003512

§ 371 (c)(1),
(2), (4) Date: Nov. 13, 2006

(87) PCT Pub. No.: WO2005/017523

PCT Pub. Date: Feb. 24, 2005

(65) Prior Publication Data

US 2007/0166758 A1 Jul. 19, 2007

(30) Foreign Application Priority Data

Aug. 15, 2003 (GB) ................... 0319167.3

(51) Int. Cl.
*G01N 33/00* (2006.01)
*G01N 33/543* (2006.01)

(52) U.S. Cl. ........................ 435/7.1; 435/7.21; 436/501; 436/518

(58) Field of Classification Search ........................ None
See application file for complete search history.

(56) References Cited

U.S. PATENT DOCUMENTS

| 4,801,531 A | 1/1989 | Frossard ........................ 435/6 |
| 5,320,945 A | 6/1994 | Dessauer et al. .............. 435/13 |
| 5,538,897 A * | 7/1996 | Yates et al. .................... 436/89 |

FOREIGN PATENT DOCUMENTS

| EP | 0927767 A3 | 8/1998 |
| WO | WO 00/52476 * | 9/2000 |
| WO | WO 01/13125 A1 | 2/2001 |
| WO | WO 01/64008 A2 | 9/2001 |

OTHER PUBLICATIONS

Kasturi et al. (Stroke, vol. 23, No. 9, 1992, pp. 1257-1264).*
A. Altes et al, *Hemostatic Disturbances in Acute Ischemic Stroke: A Study of 86 Patients*, Acta Haematol 94:10-15, 1995.
T. Kawamoto et al., *Multivalidation Analysis of the Risk Factors for Ischemic Heart Disease and Cerebral Infarction*, Jpn J Geriat 22:550-557, 1985.
A. Westman et al., *Matrix-assisted Laser Desorption/Ionization Time-of-flight Mass Spectrometry Analysis of Proteins in Human Cerebrospinal Fluid*, Rapid Commun. Mass Spectrom. 12, 1092-1098, 1998.
VP Singh, et al., *Antithrombin III Activity in Cerebrovascular Accidents*, API Textbook of Medicine 7th Edition, pp. 268-271, 2003.
Tohgi, Hideo, *Coagulation—fibrinolysis Abnormalities in Acute and Chronic Phases of Cerebral Thrombosis and Embolism*, Department of Neurology, Iwate Medical University, Stroke, 1990, vol. 21, pp. 1663-1667.

* cited by examiner

*Primary Examiner*—Lisa V Cook
(74) *Attorney, Agent, or Firm*—Arent Fox LLP

(57) ABSTRACT

Stroke is diagnosed in a subject by determining the concentration of at least one polypeptide selected from Apo C-III, Serum Amyloid A, Apo C-I, Antithrombin III fragment and Apo A-I in a sample of body fluid taken from the subject.

11 Claims, 23 Drawing Sheets

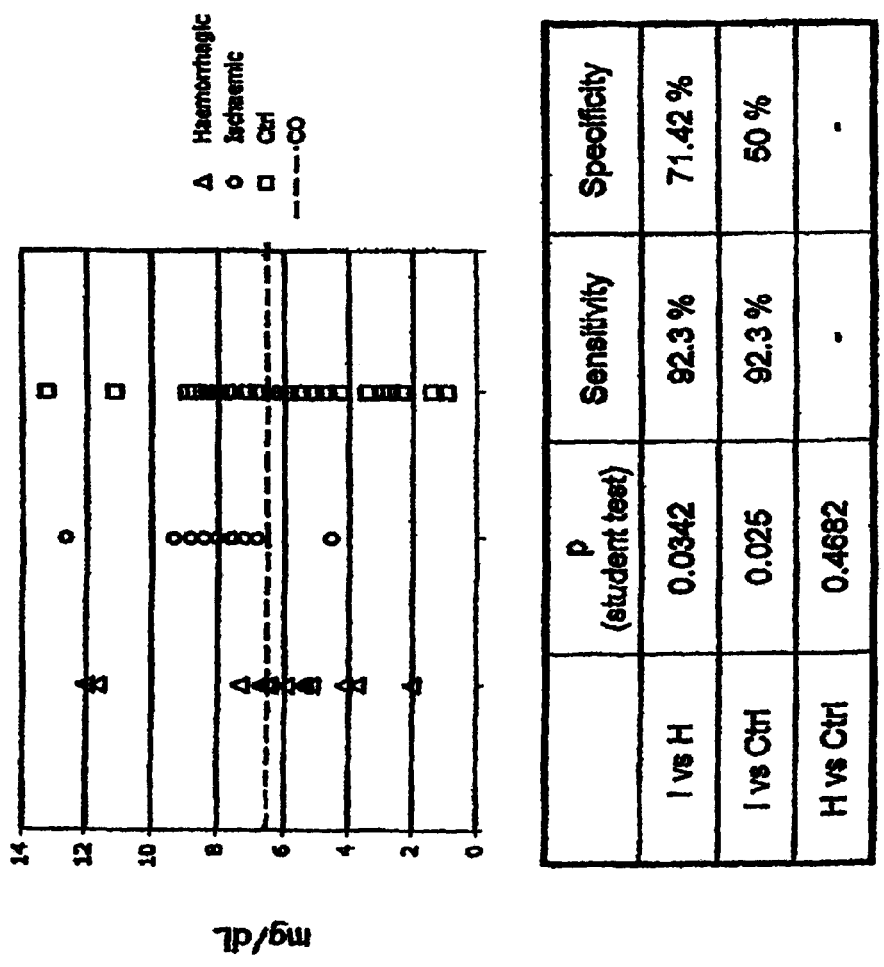
Figure 10. Determination of ApoC-III level in 14 haemorrhagic and 13 ischaemic stroke plasma samples compared to 30 negative controls using Daiichi tests (Cobas Mira plus automate)

DIAGNOSTIC METHOD FOR STROKE

RELATED APPLICATION INFORMATION

This application is a 371 national stage entry of PCT/GB04/03512, filed Aug. 16, 2004, which claims the benefit of priority from UK Application No. 0319167.3, filed on Aug. 15, 2003.

BACKGROUND OF THE INVENTION

1. Field of the Invention

This invention relates to a diagnostic method for stroke.

2. Description of the Related Art

Stroke has the third highest death-rate in industrial countries. It is caused either by bleeding in the brain from a ruptured blood vessel (haemorrhagic stroke) or by obstruction of a blood vessel in the brain (ischaemic or thrombotic stroke). Stroke results from either a permanent or a transient reduction in cerebral blood flow. This reduction in flow is, in most cases, caused by the arterial occlusion due to either an embolus or a local thrombosis. Depending on the localisation of brain injury and the intensity of necrosed neurones, stroke symptoms can become a life handicap for patients and the death rate from stroke events approaches 30%.

Recently, S100B was described as a potential biochemical marker for stroke diagnosis, see U. Missler et al., "S100 protein and neuron-specific enolase concentrations in blood as indicators of infarct volume and prognosis in acute ischemia stroke", Stroke 1997; 28:1956-60. However, S100B has also been reported as a useful marker for early detection of metastases of melanoma and cerebral complications from head injury and cardiac surgery. Thus, the sensitivity and specificity of the S100B test were limited to 44% and 67%, respectively, see M. Takahashi et al., "Rapid and sensitive immunoassay for the measurement of serum S100B using isoform-specific monoclonal antibody", Clin. Chem. 1999; 45:1307-11. Development of new stroke markers would help clinicians to establish early diagnosis.

WO 01/42793 relates to a diagnostic assay for stroke in which the concentration of heart or brain fatty acid binding protein (H-FABP or B-FABP) is determined in a sample of body fluid.

U.S. Pat. No. 6,225,047 describes the use of retentate chromatography to generate difference maps, and in particular a method of identifying analytes that are differentially present between two samples. One specific method described therein is laser desorption mass spectrometry.

WO 01/25791 describes a method for aiding a prostate cancer diagnosis, which comprises determining a test amount of a polypeptide marker, which is differentially present in samples of a prostate cancer patient and a subject who does not have prostate cancer. The marker may be determined using mass spectrometry, and preferably laser desorption mass spectrometry.

Development of new non-invasive stroke markers for body fluids and new methods of determining the markers would help clinicians to establish early diagnosis. This problem has now been solved by the present invention.

Our earlier application PCT/EP03/01462 (WO 03/069346) discloses a method of diagnosis of stroke or the possibility thereof in a subject suspected of suffering from stroke, which comprises subjecting a sample of body fluid taken from the subject to mass spectrometry, thereby to determine a test amount of a polypeptide in the sample, wherein the polypeptide is differentially contained in the body fluid of stroke-affected subjects and non-stroke-affected subjects, and has a molecular weight in the range of from 3000 to 30000; and determining whether the test amount is consistent with a diagnosis of stroke. In a preferred embodiment the mass spectrometry involves surface-enhanced laser desorption/ionisation (SELDI).

SUMMARY OF THE INVENTION

We have further investigated the mass spectrometry (SELDI) peaks in our earlier application, by the procedures described in Examples 4-9 below, which relate to the identification and immuno validation of stroke markers. As a result have found that certain polypeptides are useful markers in the diagnosis of stroke and brain damage.

The new markers used in the present invention are as follows:

Apolipoprotein (hereinafter called Apo C-III). This is a candidate for the 11.7 kDa SELDI peak (as a glycosylated form). It has the Swiss-Prot accession number P02656, a length of 79aa, a molecular weight of 8765 Da and the following sequence:

```
21 SEAEDASLLS FMQGYMKHAT KTAKDALSSV QESQVAQQAR 60
   GWVTDGFSSL KDYWSTVKDK FSEFWDLDPE VRPTSAVAA  99
(SEQ ID NO. 1)
```

Serum amyloid A protein (SAA). This is a candidate protein for the 11.5 and 11.7 kDa SAX2 SELDI peaks. It has the Swiss-Prot accession number P02735, a length of 103aa, a molecular weight of 11682 Da and the following sequence:

```
19 RS FFSFLGEAFD GARDMWRAYS DMREANYIGS DKYFHARGNY                      60
    DAAKRGPGGV WAAEAISDAR ENIQRFFGHG AEDSLADQAA NEWGRSGKDP NHFRPAGLPE 120
    KY                                                                122
(SEQ ID NO. 2)
```

Apolipoprotein C-1 (hereinafter called Apo C-1). This is a candidate protein for the 6.44 and 6.64 kDa SAX2 SELDI peaks. It has the Swiss-Prot accession number P02654, a length of 57aa, a molecular weight of 6631 Da and the following sequence:

```
27 TPDV SSALDKLKEF GNTLEDKARE LISRIKQSEL SAKMREWFSE TFQKVKEKLK IDS 83
(SEQ ID NO. 3)
```

Antithrombin III (Fragment). This is a candidate protein for the 4.47, 4.63 and 4.80 SAX2 SELDI peaks. It has the Swiss-Prot accession number P01008, a length of 38aa, a molecular weight of 4473 Da and the following sequence:

```
426 S LNPNRVTFKA NRPFLVFIRE VPLNTIIFMG RVANPCVK 464
(SEQ ID NO. 4)
```

Apolipoprotein A-1 (hereinafter called Apo A-I). This is a candidate protein for the 28 kDa SAX2 SELDI peak. It has the Swiss-Prot accession number P02647, a length of 244 aa, a molecular weight of 28079 Da and the following sequence:

```
DEPPQS PWDRVKDLAT VYVDVLKDSG RDYVSQFEGS ALGKQLNLKL

LDNWDSVTST FSKLREQLGP VTQEFWDNLE KETEGLRQEM

SKDLEEVKAK VQPYLDDFQK KWQEEMELYR QKVEPLRAEL

QEGARQKLHE LQEKLSPLGE EMRDRARAHV DALRTHLAPY

SDELRQRLAA RLEALKENGG ARLAEYHAKA TEHLSTLSEK

AKPALEDLRQ GLLPVLESFK VSFLSALEEY TKKLNTQ
(SEQ ID NO. 5)
```

The present invention is defined in the accompanying Claims.

BRIEF DESCRIPTION OF THE DRAWINGS

FIG. 10 shows the results of determination of ApoC-III levels in 14 haemorrhagic and 13 ischaemic stroke plasma samples compared to 30 negative controls using Daiichi tests (Cobas Mira plus automate)

In FIGS. 1 to 9 and 11, the horizontal axis represents molecular weight in Da (m/z ratio), and the vertical axis represents signal intensity, i.e. amount of material having the given molecular weight.

DESCRIPTION OF PREFERRED EMBODIMENTS

Figure 1A:
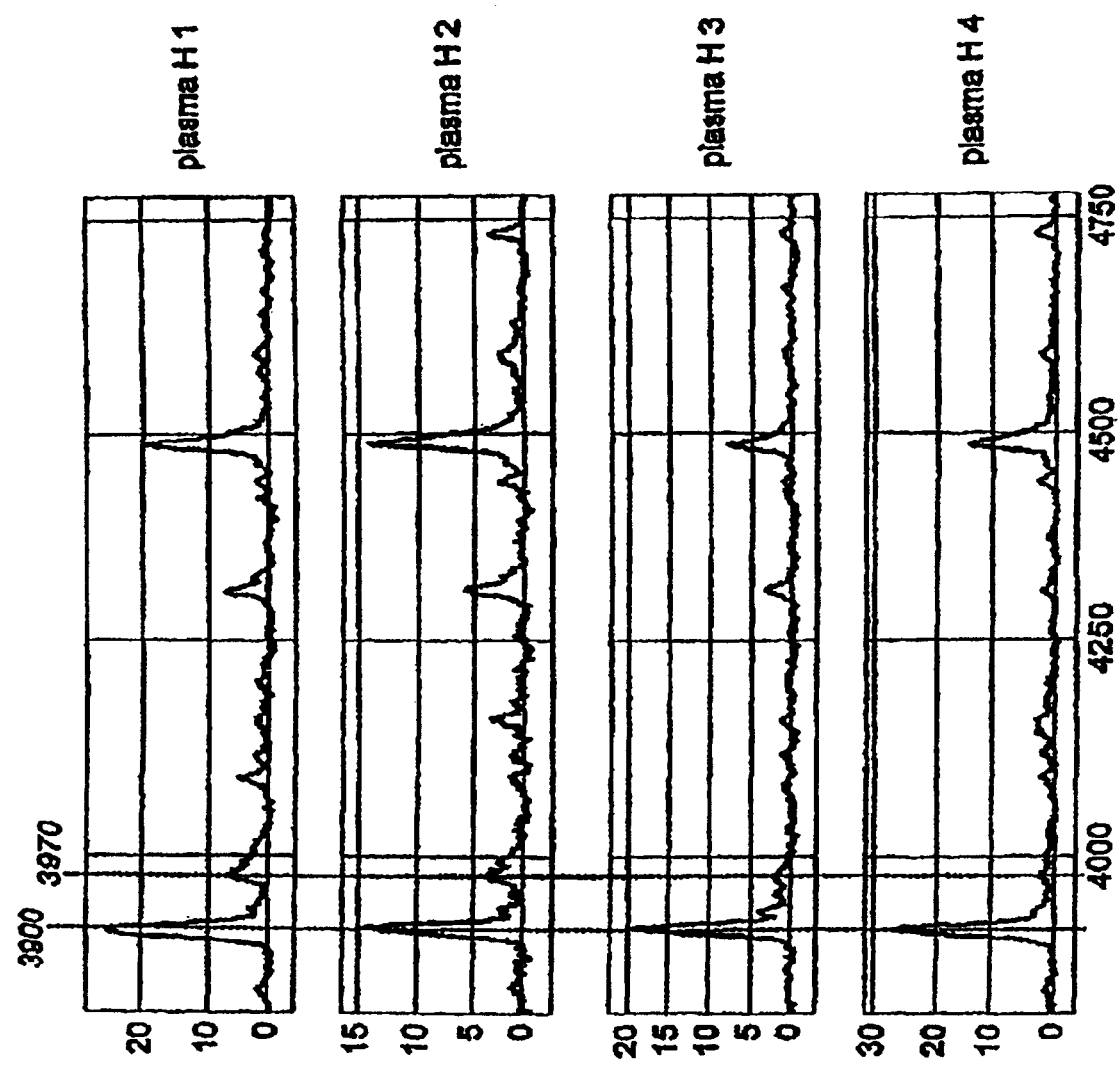
FIGS. 1 (A and B) is a spectral view of plasma from four hemorrhagic stroke patients (H 1-4) and four control samples (CTRL 1-4) using laser desorption/ionization mass spectrometry, in the molecular weight range of 3750 to 4750 Da.

The invention provides a method of diagnosis of stroke or the possibility thereof in a subject suspected of suffering from stroke, and also a method of discriminating between haemorrhagic stroke and ischaemic stroke. Where there is reference herein to diagnosis of stroke or diagnostic applications relating to stroke, it should be understood that discriminating between haemorrhagic stroke and ischaemic stroke is also included. As well as stroke, the invention enables other brain damage disorders to be diagnosed. A specific polypeptide marker selected from Apo C-III, Serum Amyloid A, Apo C-I, Antithrombin III fragment and Apo A-I is determined in a body fluid sample, for example by using an antibody thereto. The marker is preferably measured by an immunoassay, using a specific antibody to the polypeptide and measuring the extent of the antigen (polypeptide)/antibody interaction. The antibody may be a monoclonal antibody or an engineered (chimeric) antibody. Antibodies to the polypeptides are known and are commercially available. Also, the usual Köhler-Milstein method may be used to raise antibodies. Less preferably, the antibody may be polyclonal. In the context of the present invention, the term "antibodies" includes binding fragments of antibodies, such as single chain or Fab fragments.

Any known method of immunoassay may be used. In a sandwich assay an antibody (e.g. polyclonal) to the polypeptide is bound to the solid phase such as a well of a plastics microtitre plate, and incubated with the sample and with a labelled second antibody specific to the polypeptide to be detected. Alternatively, an antibody capture assay (also called "indirect immunoassay") can be used. Here, the test sample is allowed to bind to a solid phase, and the anti-polypeptide antibody (polyclonal or monoclonal) is then added and allowed to bind. If a polyclonal antibody is used in this context, it should desirably be one which exhibits a low cross-reactivity with other forms of polypeptide. After washing away unbound material, the amount of antibody bound to the solid phase is determined using a labelled second antibody, anti- to the first.

A direct assay can be performed by using a labelled anti-polypeptide antibody. The test sample is allowed to bind to the solid phase and the anti-polypeptide antibody is added. After washing away unbound material, the amount of antibody bound to the solid phase is determined. The antibody can be labelled directly rather than via a second antibody.

In another embodiment, a competition assay can be performed between the sample and a labelled polypeptide or a peptide derived therefrom, these two antigens being in competition for a limited amount of anti-polypeptide antibody bound to a solid support. The labelled polypeptide or peptide can be pre-incubated with the antibody on the solid phase, whereby the polypeptide in the sample displaces part of the polypeptide or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

Throughout, the label is preferably an enzyme. The substrate for the enzyme may be colour-forming, fluorescent or chemiluminescent. Alternatively, the label may be a radioisotope or fluorescent, e.g. using conjugated fluorescein.

The enzyme may, for example, be alkaline phosphatase or horseradish peroxidase and can conveniently be used calorimetrically, e.g. using p-nitrophenyl phosphate as a yellow-forming substrate with alkaline phosphatase.

For a chemiluminescent assay, the antibody can be labelled with an acridinium ester or horseradish peroxidase. The latter is used in enhanced chemiluminescent (ECL) assay. Here, the antibody, labelled with horseradish peroxidase, participates in a chemiluminescent reaction with luminol, a peroxide substrate and a compound which enhances the intensity and duration of the emitted light, typically 4-iodophenol or 4-hydroxycinnamic acid.

An amplified immunoassay such as immuno-PCR can be used. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 1995; 23, 522-529 (1995) or T. Sano et al., in "Molecular Biology and Biotechnology" ed. Robert A. Meyers, VCH Publishers, Inc. (1995), pages 458-460. The signal is read out as before.

In one procedure, an enzyme-linked immunosorbent assay (ELISA) can be used to detect the polypeptide.

The use of a rapid microparticle-enhanced turbidimetric immunoassay, developed for H-FABP in the case of AMI, M. Robers et al., "Development of a rapid microparticle-enhanced turbidimetric immunoassay for plasma fatty acid-binding protein, an early marker of acute myocardial infarction", Clin. Chem. 1998; 44:1564-1567, significantly decreases the time of the assay. Thus, the full automation in a widely used clinical chemistry analyser such as the COBAS™ MIRA Plus system from Hoffmann-La Roche, described by M. Robers et al. supra, or the AxSYM™ system from Abbott Laboratories, should be possible and applied for routine clinical diagnosis of stroke.

The polypeptide concentrations can be measured by other means than immunoassay. For example, the sample can be subjected to 2D-gel electrophoresis and the amount of the polypeptide estimated by densitometric scanning of the gel or of a blot therefrom. However, it is desirable to carry out the assay in a rapid manner, so that the patient can be treated promptly.

The polypeptide can also be determined by mass spectrometry, as described in our earlier application PCT/EP03/01462 (WO 03/069346). A sample of body fluid taken from the subject is subjected to mass spectrometry, to determine the presence or absence in the sample of a polypeptide marker which is differentially contained in the body fluid of stroke-affected subjects and non-affected subjects. The polypeptide marker has a molecular weight in the range of from 3000 to 30000, preferably from 3900 to 29000, and the presence or absence of the marker is indicative of stroke. A particular feature of the invention is that the presence or absence of certain markers can be used to determine whether a diagnosed stroke is of the ischaemic or haemorrhagic type.

The term polypeptide includes proteins and protein fragments, as well as peptides modified by the addition of non-peptide residues, e.g. carbohydrates, phosphates, sulfates or any other post-translational modification.

The sample may be adsorbed on a probe under conditions which allow binding between the polypeptide and adsorbent material on the probe. The adsorbent material preferably comprises a metal chelating group complexed with a metal ion, and a preferred metal is copper. Prior to detecting the polypeptide, unbound or weakly bound materials on the probe may be removed with a washing solution, thereby enriching the polypeptide in the sample. The sample is preferably adsorbed on a probe having an immobilised metal affinity capture (IMAC) or a strong anion exchange (SAX) surface capable of binding the polypeptide. The sample may be also adsorbed on a probe having hydrophobic, strong anionic or weak cationic exchange surfaces under conditions which allow binding of the polypeptides. The probe may consist of a strip having several adsorbent wells, and be inserted into the spectrometer, then movable therein so that each well is in turn struck by the ionizing means (e.g. laser) to give a spectrometer reading. The polypeptide is preferably determined by surface-enhanced laser desorption/ionisation (SELDI) and time of flight mass spectrometry (TOF-MS).

In principle, any body fluid can be used to provide a sample for diagnosis, but preferably the body fluid is cerebrospinal fluid (CSF), plasma, serum, blood, urine or tears.

In one embodiment, one or more polypeptides having a respective molecular weight of about 3900, about 3970, about 3990, about 6945, about 10070, about 14040 and/or about 28000 is determined, and increase or reduction, relative to a control, of peaks corresponding to such polypeptides is indicative of stroke. The 3900 peak is mostly higher than the 3970 and 3990 peaks in stroke plasma samples.

In another embodiment, one or more polypeptides having a respective molecular weight of about 5920, about 6660 and/or about 7770 is determined, and increase or reduction, relative to a control, of peaks corresponding to such polypeptides is indicative of stroke.

In a further embodiment, one or more polypeptides having a respective molecular weight of about 3900, about 3970, about 3990, about 14040 and/or about 28000 is determined, and increase or reduction, relative to a control, of peaks corresponding to such polypeptides is used to indicate whether a diagnosed stroke is of the ischaemic or haemorrhagic type.

Generally, the following observations, separately or in any combination, are characteristic of haemorrhagic stroke (when compared to a control): decrease of a peak at about 3970; decrease of a peak at about 5920 and/or about 10070; increase of a peak at about 6660 and/or about 6945 and/or about 7770; and decrease of a peak at about 14040 and/or about 28000.

Generally, the following observations, separately or in any combination, are characteristic of ischaemic stroke (when compared to a control): a peak at about 3970 greater than a peak at about 3990, but both lower than a peak at about 3900; decrease of a peak at about 5920 and/or about 10070; increase of a peak at about 7770; and no decrease of peaks at about 14040 and/or about 28000.

In a further embodiment, one or more polypeptides having a respective molecular weight of about 4475, about 4634 and/or about 4797 is determined, and reduction, relative to a control, of peaks corresponding to such polypeptides is indicative of stroke.

In a still further embodiment, one or more polypeptides having a respective molecular weight of about 6441 and/or about 6643 is determined, and increase, relative to a control, of peaks corresponding to such polypeptides is indicative of stroke.

In a yet further embodiment, one or more polypeptides having a respective molecular weight of about 11530 and/or about 11712 is determined, and reduction, relative to a control, of peaks corresponding to such polypeptides is indicative of stroke.

In another embodiment, a polypeptide having a molecular weight of about 28130 is determined, and increase, relative to a control, of a peak corresponding to such polypeptide is indicative of stroke.

According to the invention, a diagnosis of stroke may be made from determination of a single polypeptide or any combination of two or more of the polypeptides.

Measurement of the molecular weight of the polypeptide or polypeptides is effected in the mass spectrometer. The molecular weights quoted above can be measured with an accuracy of better than 1%, and preferably to within about 0.1%. The term "about" in connection with molecular weights therefore means within a variation of about 1%, preferably within about 0.1%, above or below the quoted value.

The invention also relates to the use of one or more of the specified polypeptides which is differentially contained in a body fluid of stroke-affected subjects and non-stroke-affected subjects, for diagnostic, prognostic and therapeutic applications. This may involve the preparation and/or use of a material which recognizes, binds to or has some affinity to the above-mentioned polypeptide. Examples of such materials are antibodies and antibody chips. The term "antibody" as used herein includes polyclonal antiserum, monoclonal antibodies, fragments of antibodies such as Fab, and genetically engineered antibodies. The antibodies may be chimeric or of a single species. The above reference to "prognostic" applications includes making a determination of the likely course of a stroke by, for example, measuring the amount of the above-mentioned polypeptide in a sample of body fluid. The above reference to "therapeutic" applications includes, for example, preparing materials which recognize, bind to or have affinity to the above-mentioned polypeptides, and using such materials in therapy. The materials may in this case be modified, for example by combining an antibody with a drug, thereby to target the drug to a specific region of the patient.

The methodology of this invention can be applied to the diagnosis of any kind of stroke. Body fluid samples are prepared from stroke-affected and non-stroke-affected subjects. The samples are applied to a probe having a surface treated with a variety of adsorbent media, for differential retention of peptides in the sample, optionally using washing liquids to remove unbound or weakly bound materials. If appropriate, energy-absorbing material can also be applied. The probe is then inserted into a mass spectrometer, and readings are taken for the various sample/adsorbent combinations using a variety of spectrometer settings. Comparison of the affected and non-affected samples under a given set of conditions reveals one or more polypeptides which are differentially expressed in the affected and non-affected samples. The presence or absence of these polypeptides can then be used in the testing of a fluid sample from a subject under the same conditions (adsorbent, spectrometer settings etc.) to determine whether or not the subject is affected. Furthermore, by comparing, on the one hand, haemorrhagic stroke samples with a control, and, on the other hand, ischaemic stroke samples with a control, it is possible to discriminate between the possibility of haemorrhagic stroke or ischaemic stroke by testing a body fluid sample from a patient under the same conditions.

The above reference to "presence or absence" of a polypeptide should be understood to mean simply that there is a significant difference in the amount of a polypeptide which is detected in the affected and non-affected sample. Thus, the "absence" of a polypeptide in a test sample may include the possibility that the polypeptide is actually present, but in a significantly lower amount than in a comparative test sample. According to the invention, a diagnosis can be made on the basis of the presence or absence of a polypeptide, and this includes the presence of a polypeptide in a significantly lower or significantly higher amount with reference to a comparative test sample.

Kits and assay devices for use in diagnosis of stroke are also within the scope of the invention. These may include one or more antibodies to a polypeptide selected from Apo C-III, Serum Amyloid A, Apo C-I, Antithrombin III fragment and Apo A-I. The antibodies will bind to the appropriate polypeptides in a fluid sample taken from a patient. The antibodies may be immobilised on a solid support. Preferably, each antibody is placed in a unique addressable location, thereby to permit a separate assay readout for each individual polypeptide in the sample, as well as readouts for any selected combination of polypeptides.

Kits for the assay of Apo C-III, Serum Amyloid A, Apo C-I, Antithrombin III fragment and Apo A-I have previously been described. However, their use for diagnosis of stroke is novel and first disclosed in the present specification. Examples of such kits are the following:

Instruchemie provide kits from Daiichi Pure Chemicals Co., Ltd. (Tokyo, Japan) for detection of ApoCIII (Turbidimetric and/or nephelometric method, ref. 241871, kit that we used) and ApoAI (Turbidimetric and/or nephelometric method, ref 2611).

Human Apolipoprotein LINCOplex Kit, Catalog #APO-62K is a multiplex assay kit manufactured by LINCO Research, Inc. and can be used for the simultaneous quantification of the following six apolipoproteins in any combinations: Apo AI, Apo AII, Apo B, Apo CII, Apo CIII, and Apo E. This kit can be used for the analysis of the above apolipoproteins in serum, plasma, tissue extract, other biological fluids, or tissue culture samples.

With regard to SAA determination, Dade Behring provide in vitro diagnostic reagents for the quantitative determination of serum amyloid A (SAA) in human serum as well as heparinized and EDTA plasma by means of particle-enhanced Immunonephelometry using the BN Systems: N Latex SAA-Catalog OQMP11. A diagnostic kit is also commercially available from Dade Behring for the detection of ApoAI.

Many kits exist for the detection of total antithrombin III, and for the determination of the activity of antithrombin III. Dade Behring provide a kit for in vitro diagnostic reagents for the quantitative determination of antithrombin III in human plasma with the BN Systems: N Antiserum to Human Antithrombin III Catalog OSAY09.

Concerning ApoCI, many mono and polyclonal antibodies are commercially available.

The following Examples illustrate the invention.

Example 1

The objective of the present study was to detect specific polypeptides in body fluids (cerebrospinal fluid, plasma and others) of stroke-affected patients. Samples were analysed by the Surface Enhanced Laser Desorption Ionization (SELDI) Mass Spectroscopy (MS) technology. This technology encompasses micro-scale affinity capture of proteins by using different types of retentate chromatography and then analysis by time of flight mass spectrometry. Difference maps are thus generated each corresponding to a typical protein profiling of given samples that were analysed with a Ciphergen Biosystem PBS II mass spectrometer (Freemont, Calif., USA). Differential expressed peaks were identified when comparing spectra generated in a group of plasma samples from stroke-affected patients with a control group of non-affected patients.

The SELDI analysis was performed using 2 μl of crude human plasma samples in order to detect specific polypeptides with metal affinity. An immobilized copper affinity array (IMAC-$Cu^{++}$) was employed in this approach to capture proteins with affinity for copper to select for a specific subset of proteins from the samples. Captured proteins were directly detected using the PBSII Protein Chip Array reader (Ciphergen Biosystems, Freemont, Calif., USA).

The following protocol was used for the processing and analysis of ProteinChip arrays using Chromatographic TED-Cu(II) adsorbent array. TED is a (tris(carboxymethyl)ethylenediamine-Cu) adsorbent coated on a silicon oxide-coated stainless steel substrate.

- The surface was first loaded with 10 µl of 100 mM copper sulfate to each spot and incubated for 15 minutes in a wet chamber.
- The chip was thereafter washed by two quick rinses with deionized water for about 10 seconds to remove the excess unbound copper.
- Before loading the samples, the I-MAC 3 array was equilibrated once with 5 µl of PBS NaCl 0.5 M for 5 minutes. After removing the equilibration buffer, 3 µl of the same buffer were added before applying 2 µl of plasma. The chip was incubated for 20 minutes in a wet chamber.
- The samples were thereafter removed and the surface was washed three times with the equilibration buffer (5 minutes each).
- Two quick final rinses with water were performed.
- The surface was allowed to air dry, followed by the addition of 0.5 µl of saturated sinapinic acid (SPA, Ciphergen Biosystem) prepared in 50% acetonitrile, 0.5% trifluoroacetic acid.
- The chip was air dried again before analysis of the retained protein on each spot with laser desorption/ionization time-of-flight mass spectrometry.
- The protein chip array was inserted into the instrument and analysed once the appropriate detector sensitivity and laser energy have been established to automate the data collection.
- The obtained spectra were analysed with the Biomark Wizard software (Ciphergen Biosystems, Freemont, Calif., USA) running on a Dell Dimension 4100 PC. It generates consistent peak sets across multiple spectra.

Figure 1B:
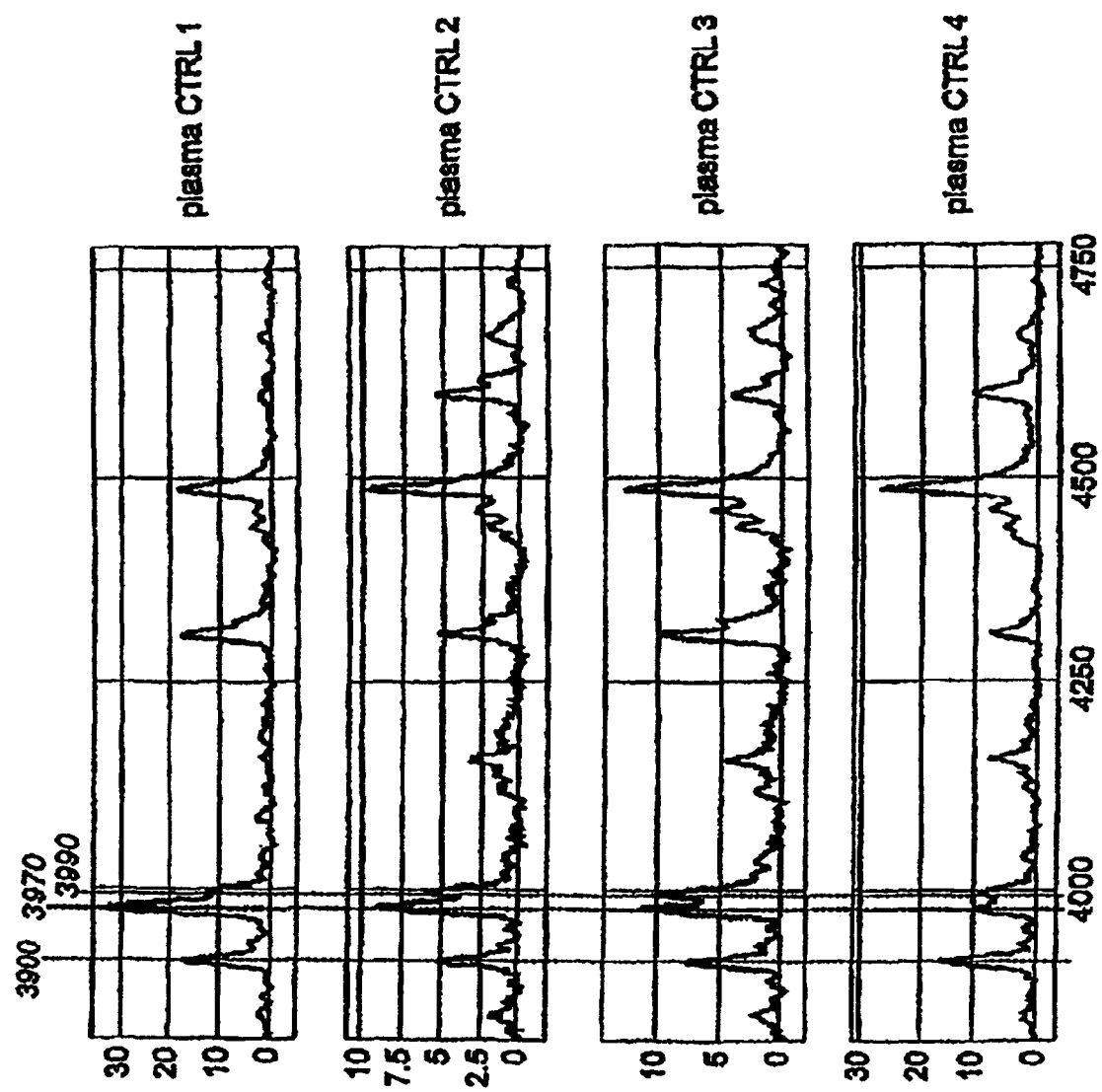
Figure 2A:
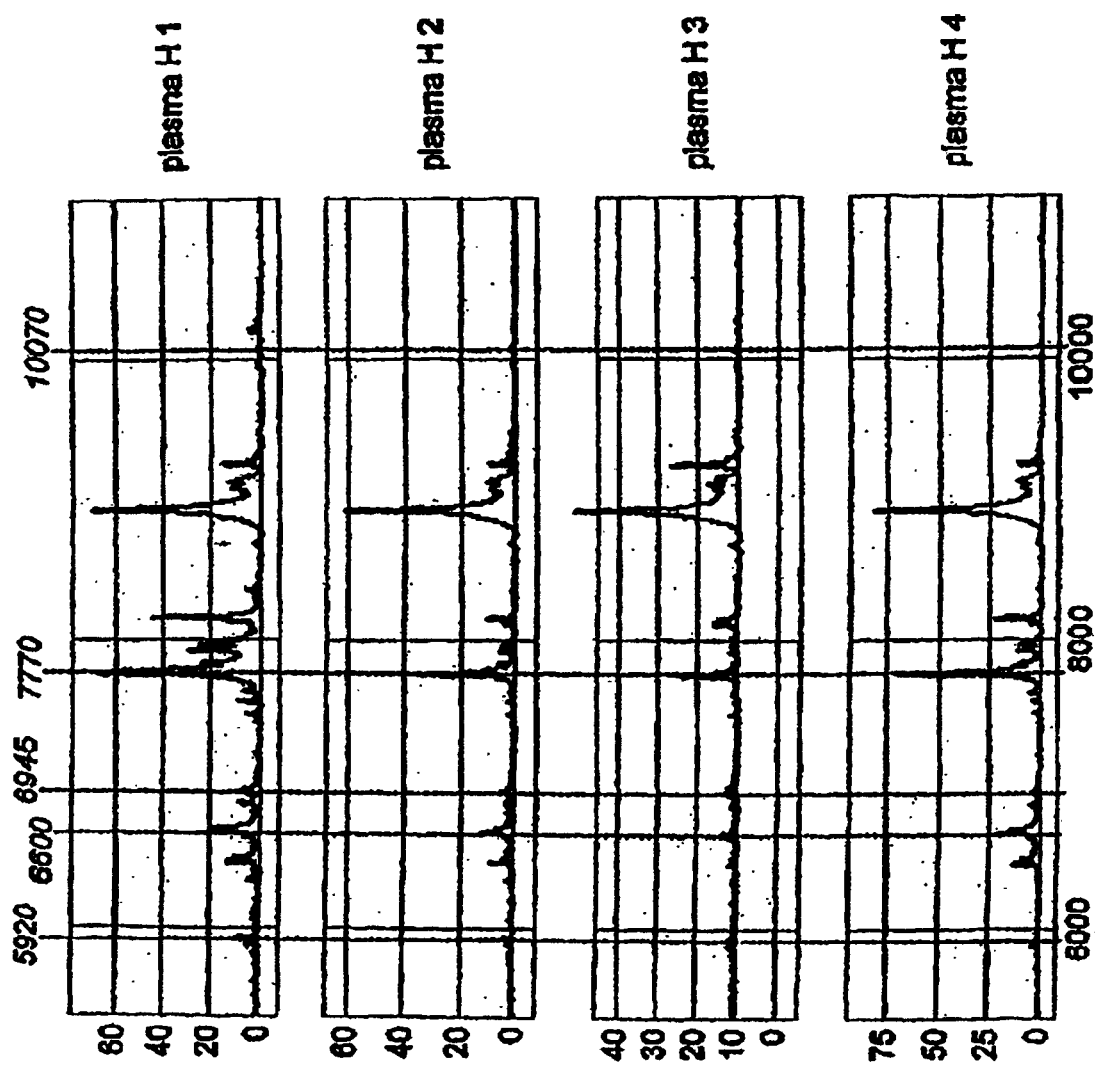
FIGS. 2 (A and B) is a view corresponding to FIG. 1, but in the molecular weight range of 5000 to 11000 Da.
Figure 2B:
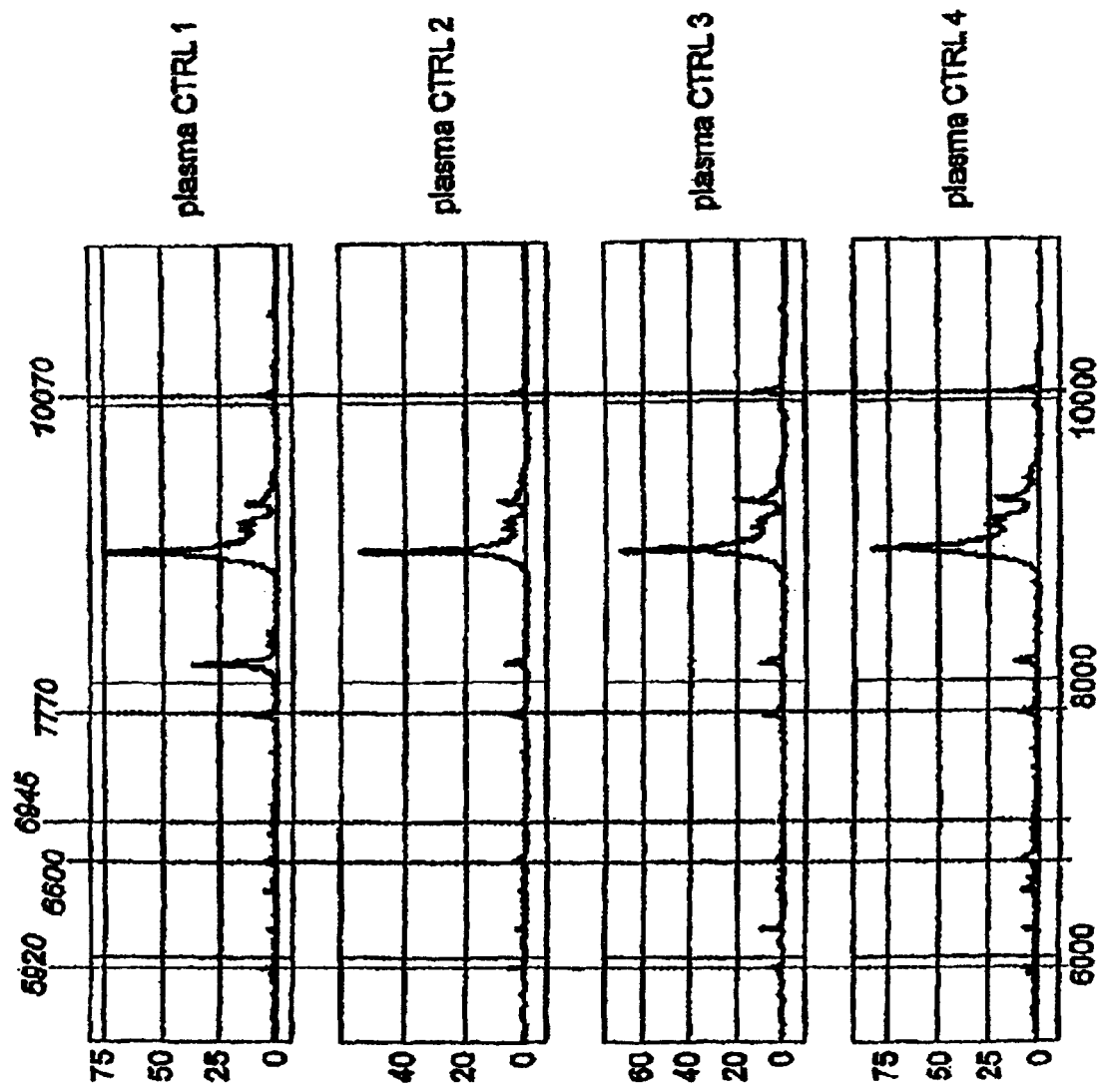
Figure 3A:
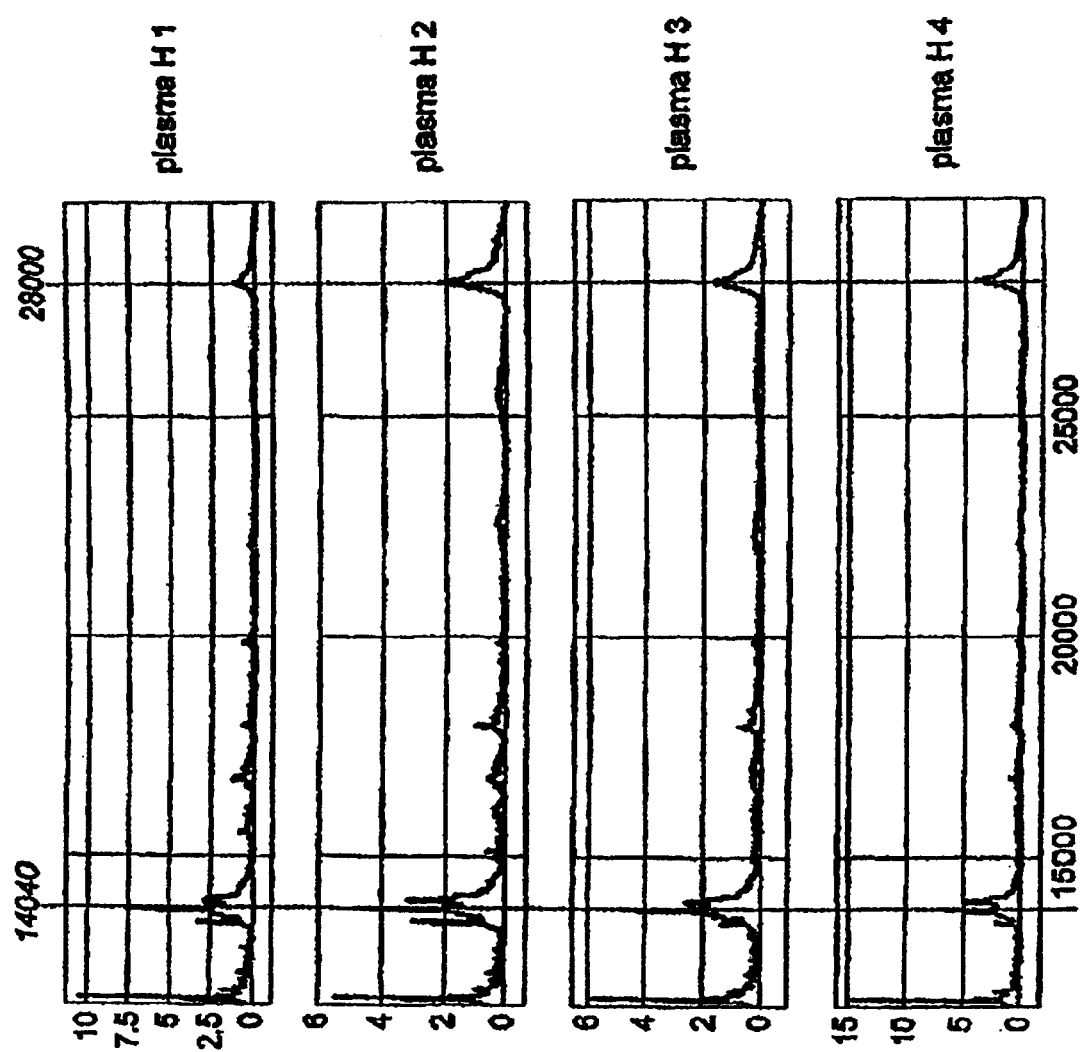
FIGS. 3 (A and B) is a view corresponding to FIG. 1, but in the molecular weight range of 12000 to 30000 Da.
Figure 3B:
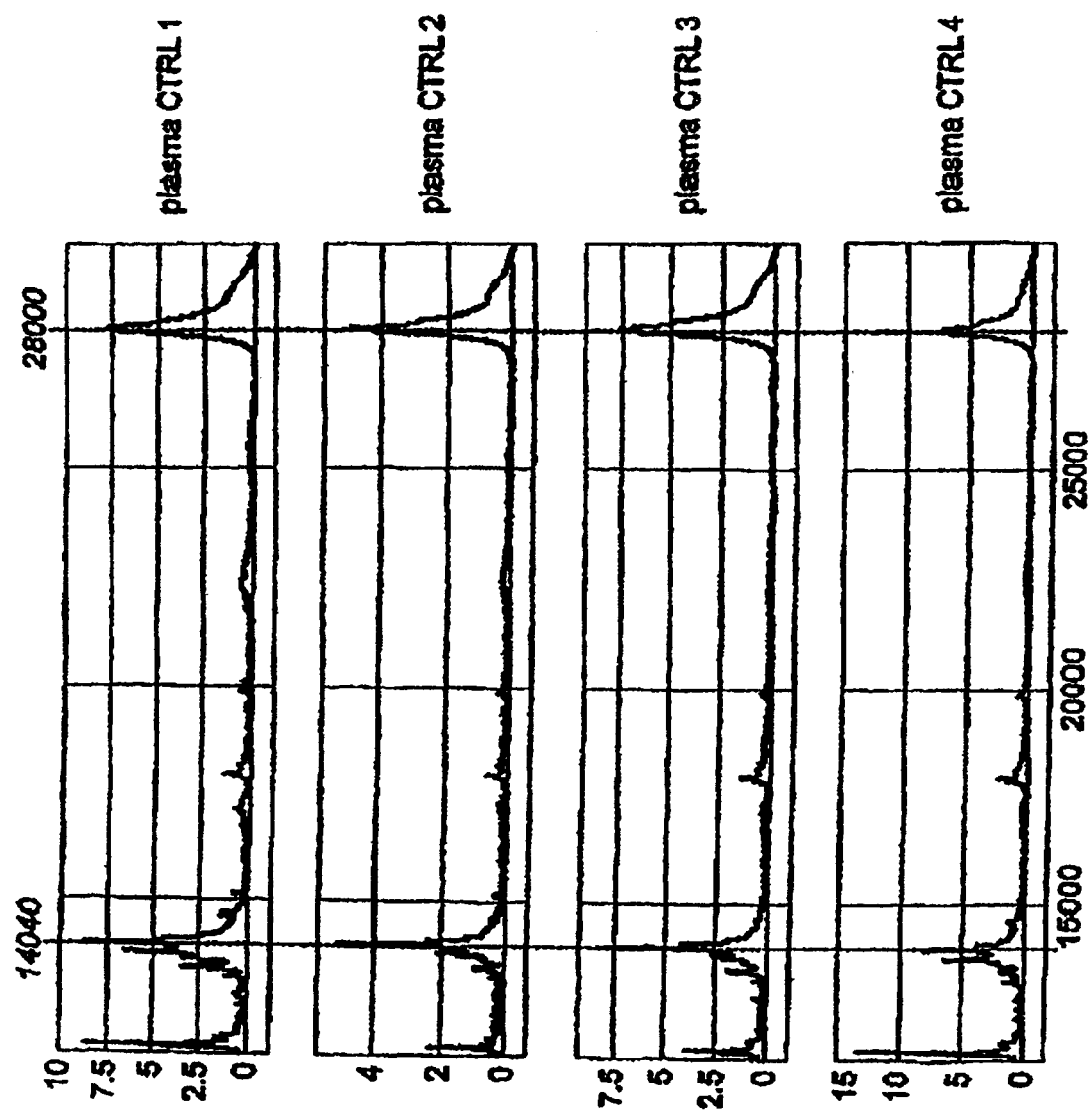

The results of the above tests on four plasma samples from haemorrhagic stroke patients (plasma H 1-4) and four plasma samples from non-affected subjects (plasma CTRL 1-4) are shown in FIGS. 1 to 3. FIG. 1 shows the strong decrease of a peak around 3970 Da in haemorrhagic samples as compared to healthy ones. In the control samples it forms a pair with a peak at about 3990, but in the haemorrhagic stroke samples the pair have nearly disappeared behind the peak at about 3900, which has been strongly increased. FIG. 2 highlights the decrease of two peaks around 5920 and 10070 in haemorrhagic stroke samples as compared to healthy ones. FIG. 2 also shows the increase of peaks at about 6660, 6945 and 7770 Da in haemorrhagic stroke samples as compared to healthy ones. FIG. 3 shows a decreased intensity of peaks at about 14040 and 28000 Da in haemorrhagic stroke samples as compared to healthy ones.

Example 2

Figure 4A:
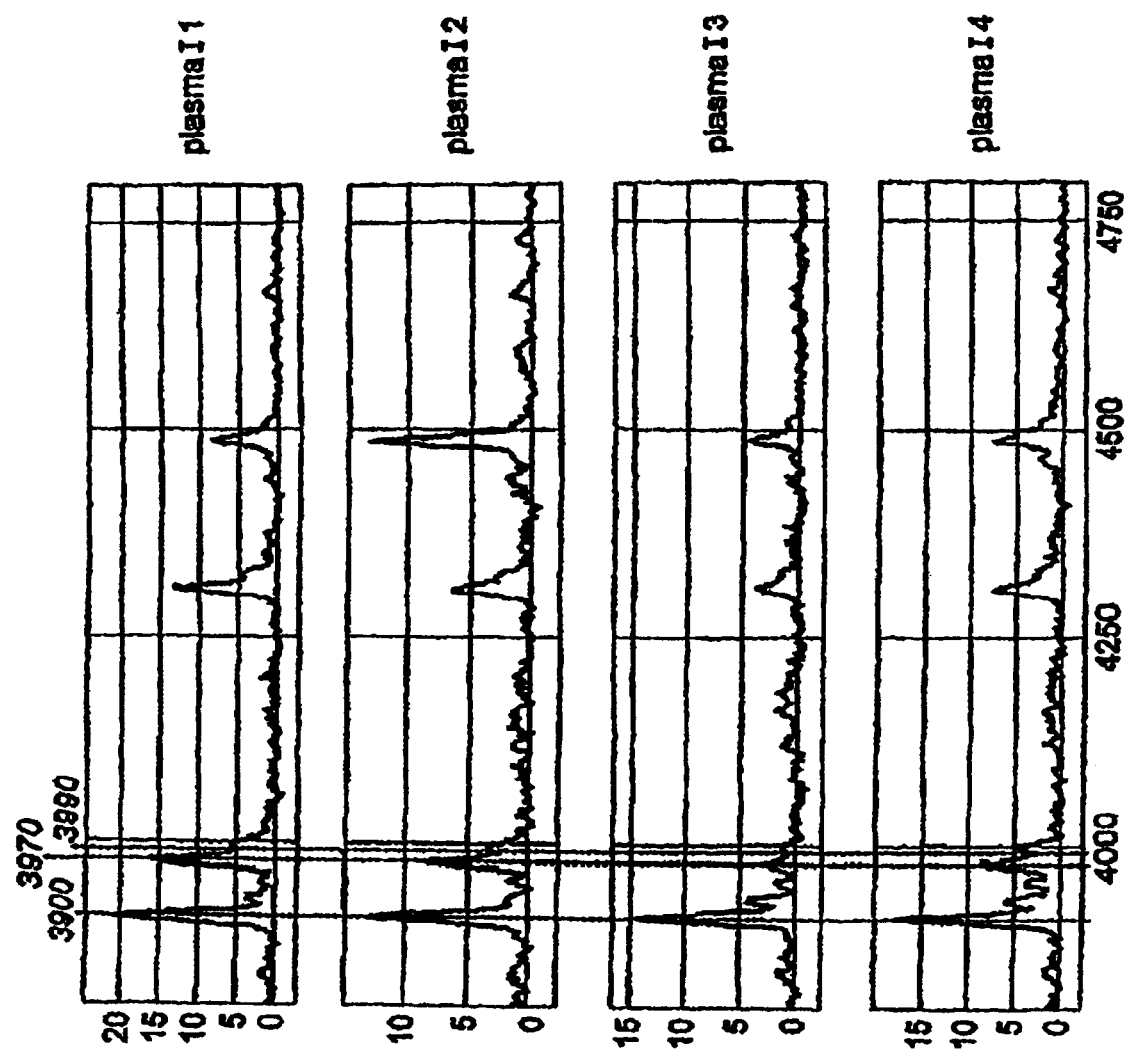
FIGS. 4 (A and B) is a spectral view of plasma from four ischaemic stroke patients (I 1-4) and four control samples (CTRL 1-4) using laser desorption/ionization mass spectrometry, in the molecular weight range of 3750 to 4750 Da.
Figure 4B:
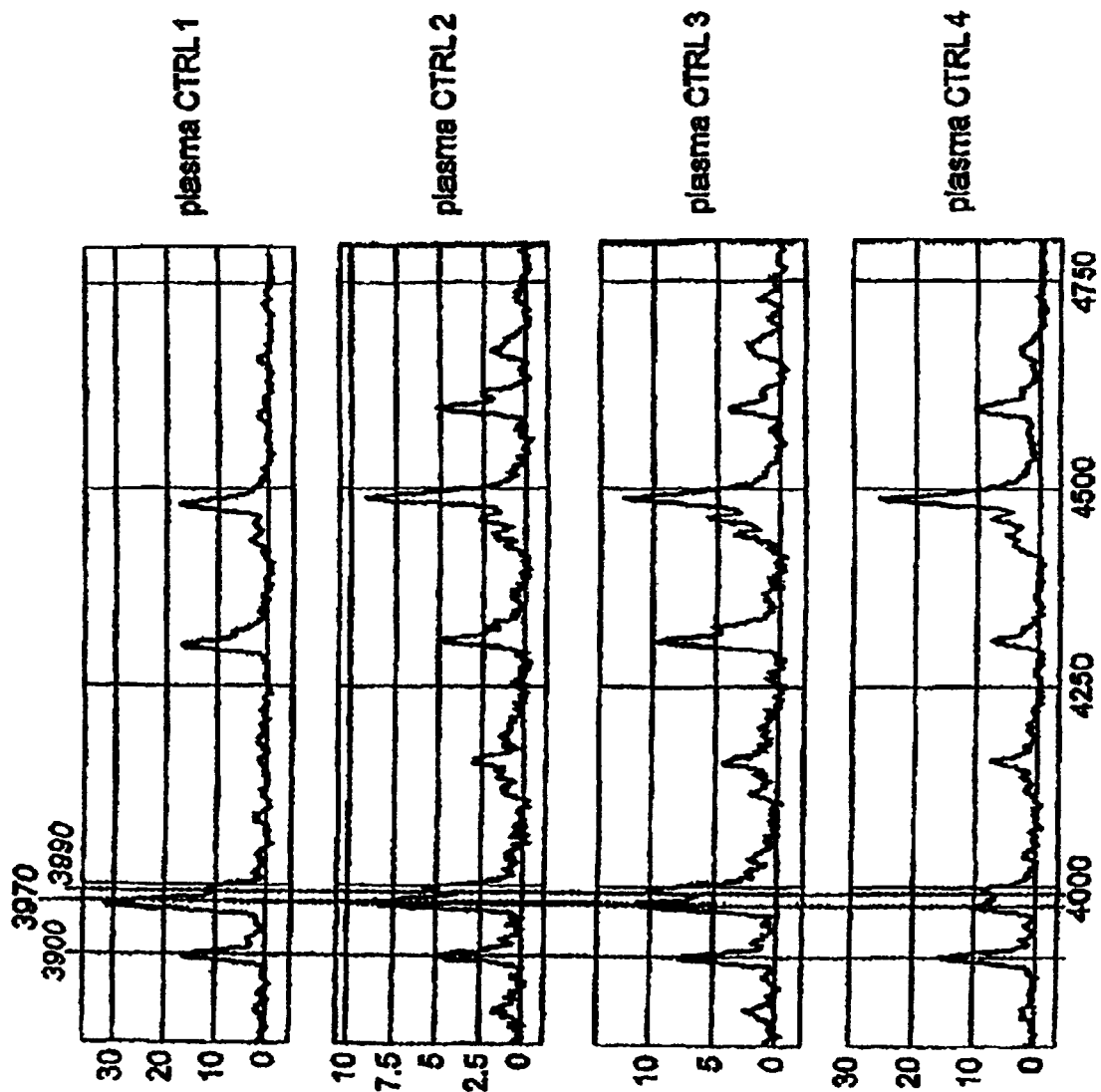
Figure 5A:
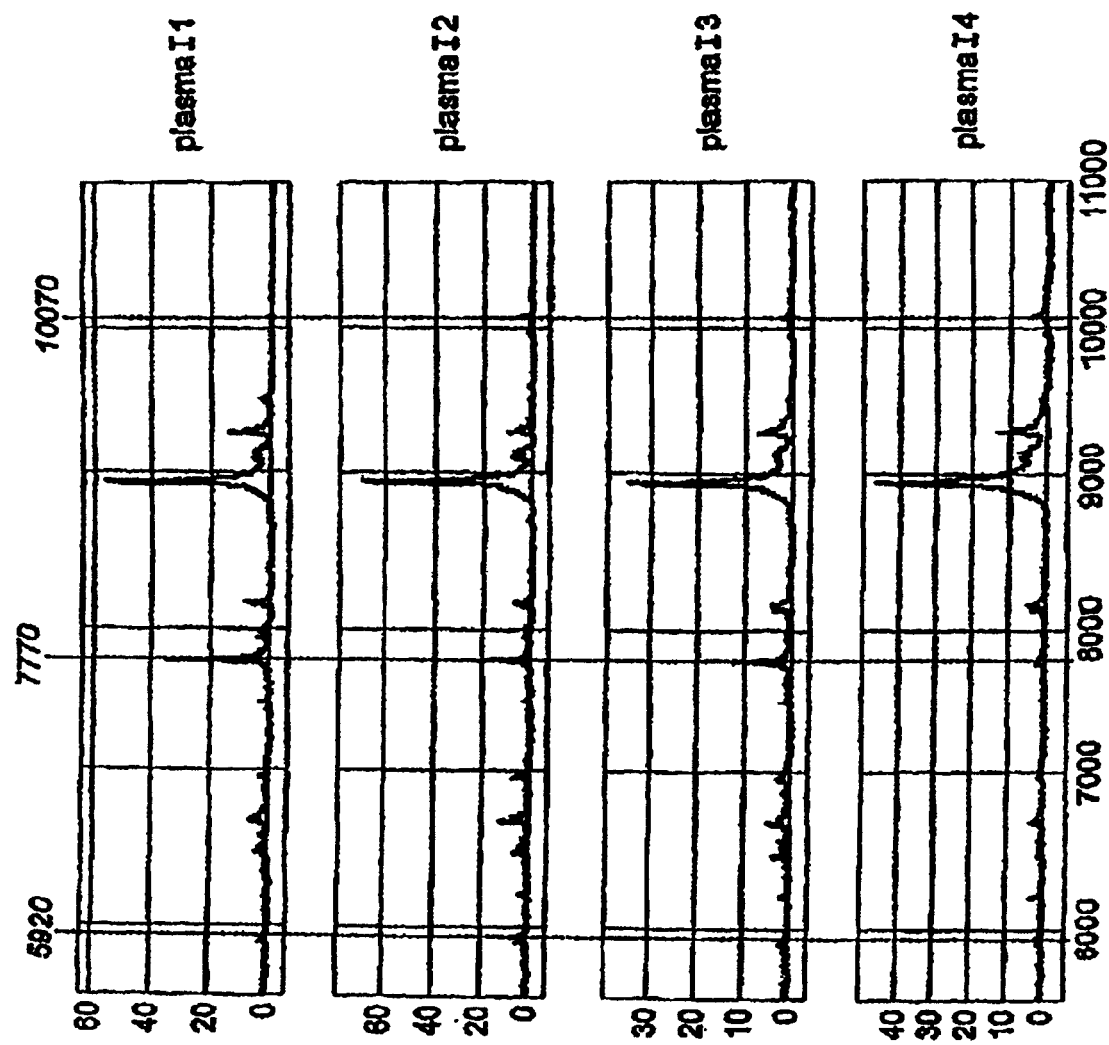
FIGS. 5 (A and B) is a view corresponding to FIG. 4, but in the molecular weight range of 5000 to 11000 Da.
Figure 5B:
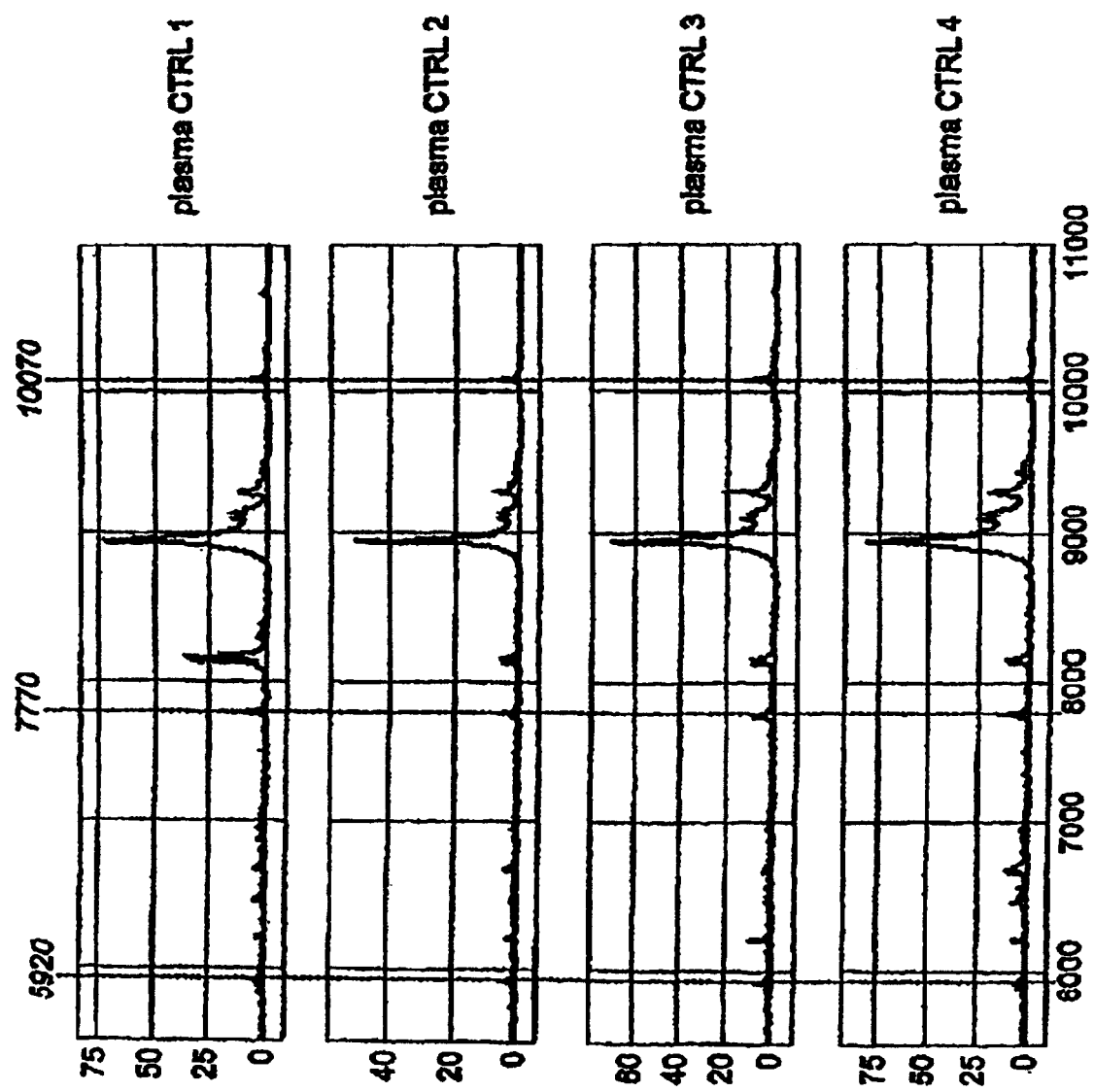
Figure 6A:
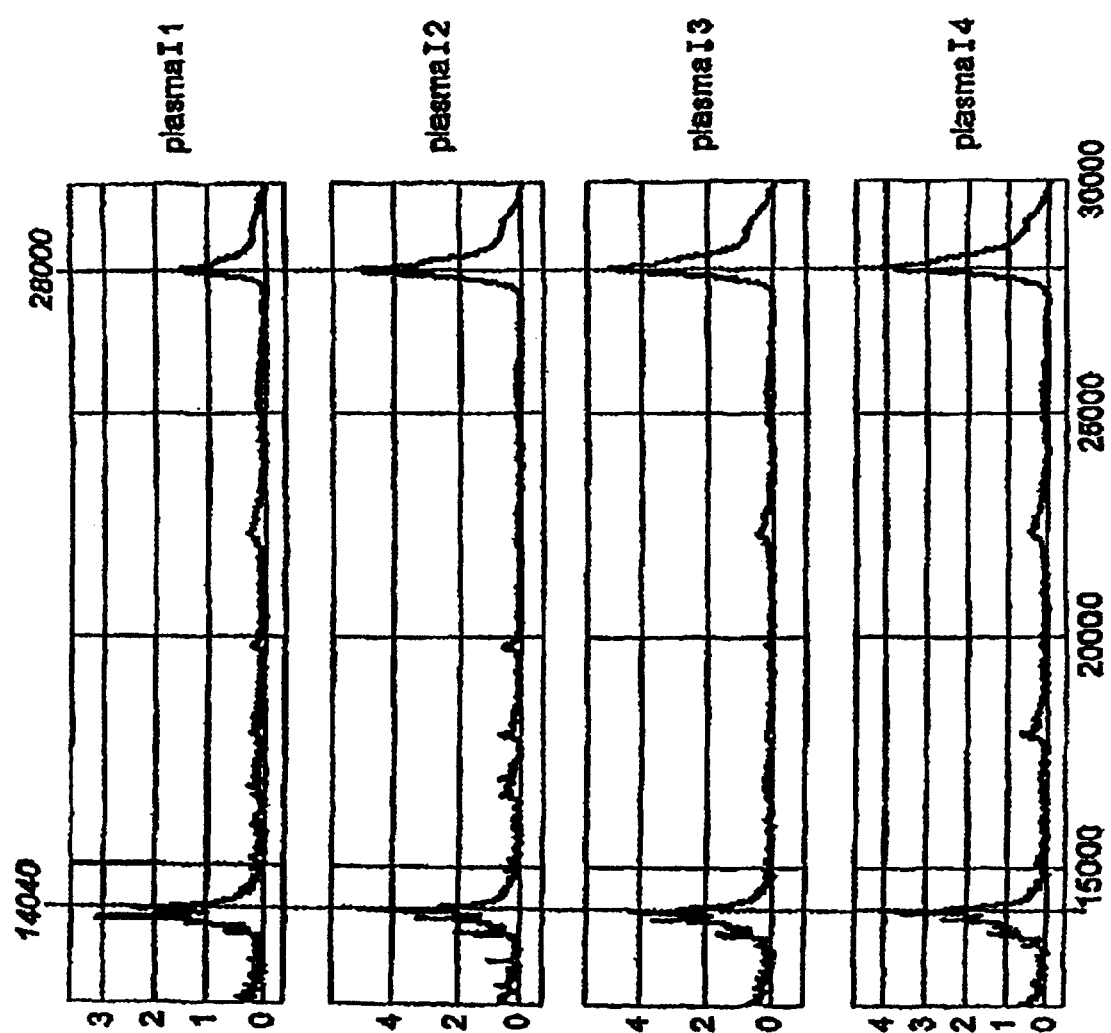
FIGS. 6 (A and B) is a view corresponding to FIG. 4, but in the molecular weight range of 12000 to 30000 Da.
Figure 6B:
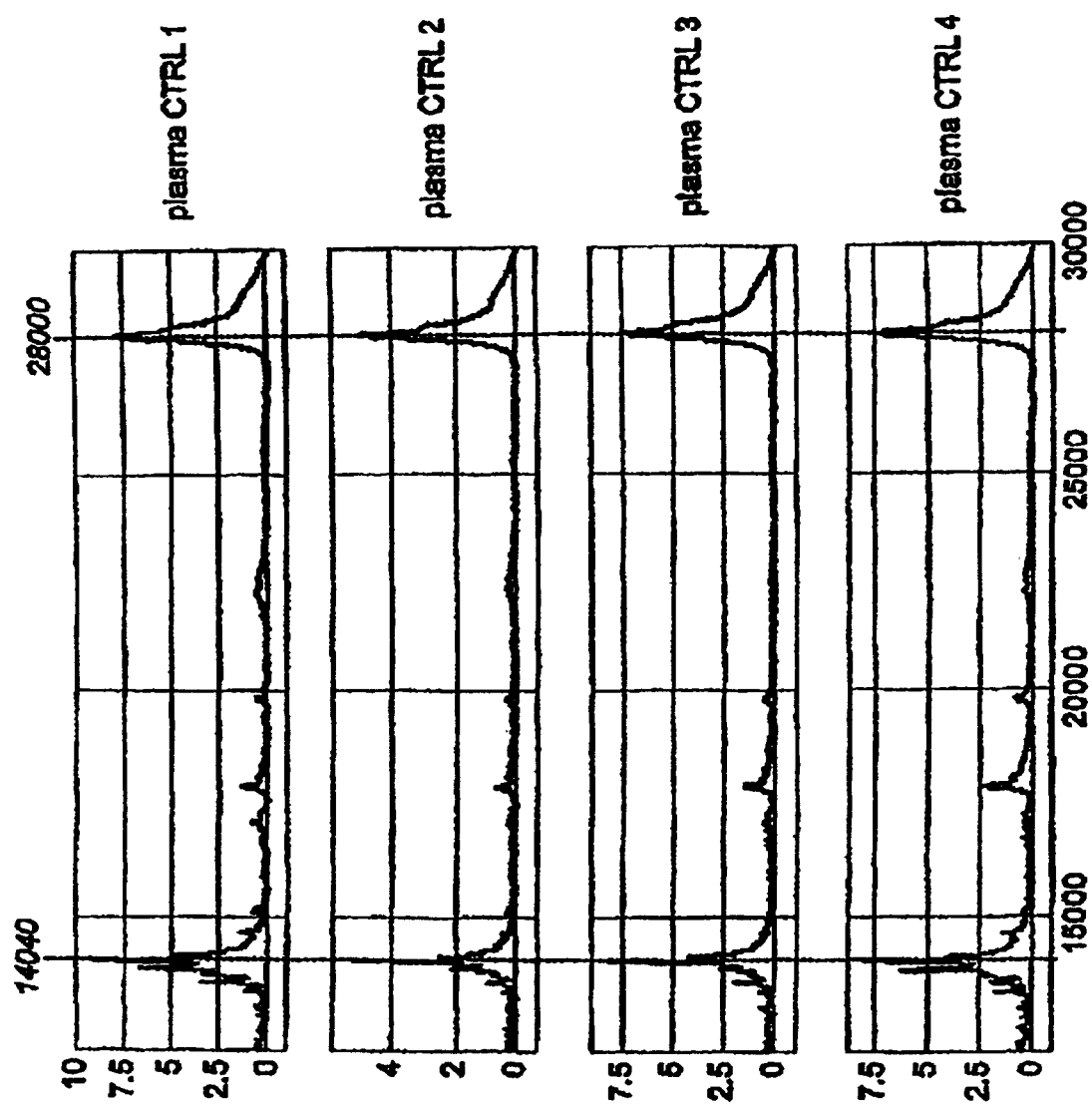

The procedure of Example 1 is repeated on four plasma samples from ischaemic stroke patients (plasma I 1-4) and four plasma samples from non-affected subjects (plasma CTRL 1-4). The results are shown in FIGS. 4 to 6. FIG. 4 shows for the ischaemic stroke samples a pair of peaks at 3970 and 3990, where the 3970 peak is higher than the 3990 peak, but of a lower intensity than the 3900 peak, in contrast to the control samples. FIG. 5 highlights the decrease of two peaks around 5920 and 10070 in ischaemic stroke samples as compared to healthy ones. FIG. 5 also shows the 7770 peak increased in ischaemic stroke samples, but to a lesser extent than in haemorrhagic stroke samples. FIG. 6 does not show any decrease of peaks around 14040 and 28000 Da between ischaemic stroke samples and healthy samples, in contrast to the differences shown for haemorrhagic stroke samples in FIG. 3.

Example 3

Figure 7A:
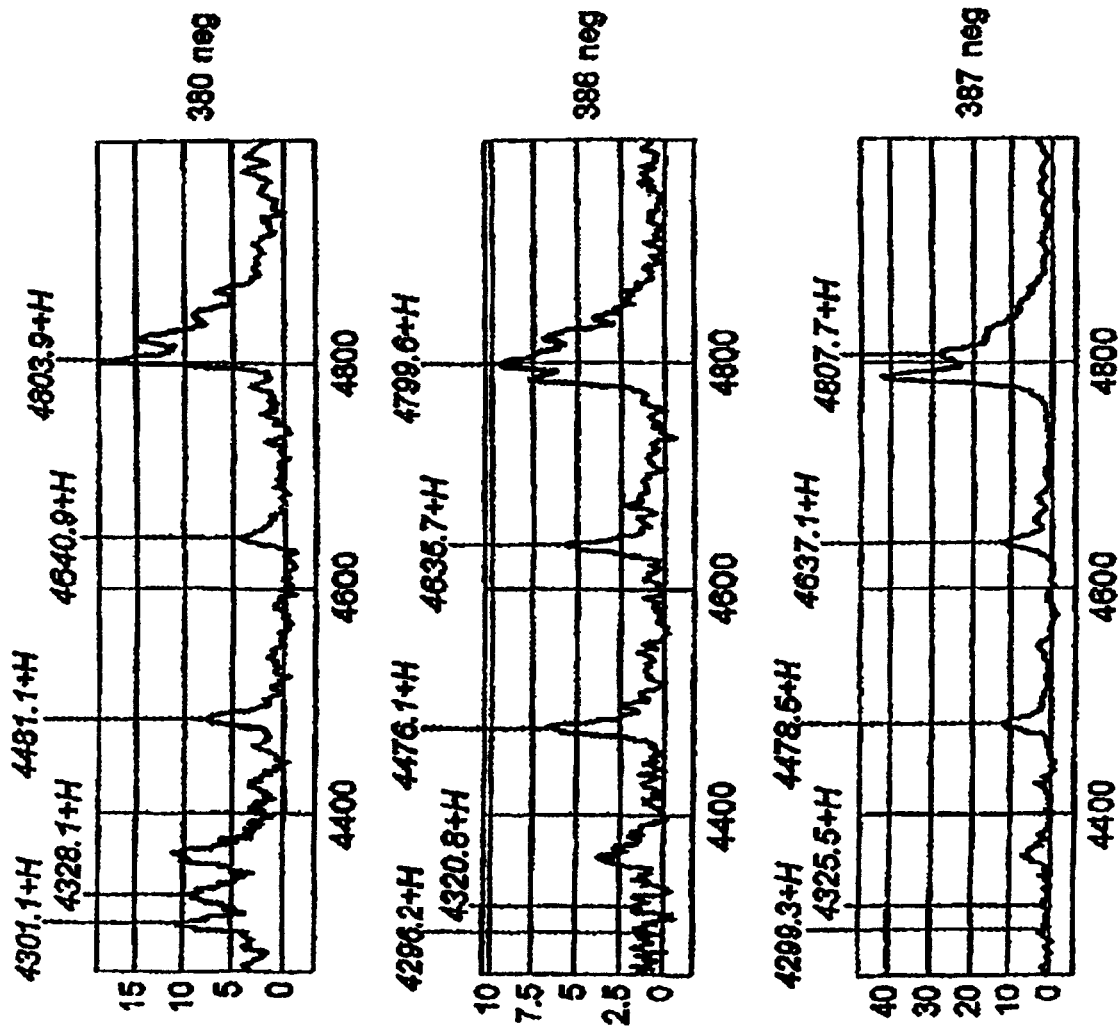
FIGS. 7 (A, B and C) is a spectral view of plasma from four stroke patients (identified as 155 stroke, 184 stroke, 194 stroke and 195 stroke) and four control samples (identified as 380 neg, 386 neg, 387 neg and 390 neg) using laser desorption/ionization mass spectrometry, in the molecular weight range of about 4300 to 5000 Da.
Figure 7B:
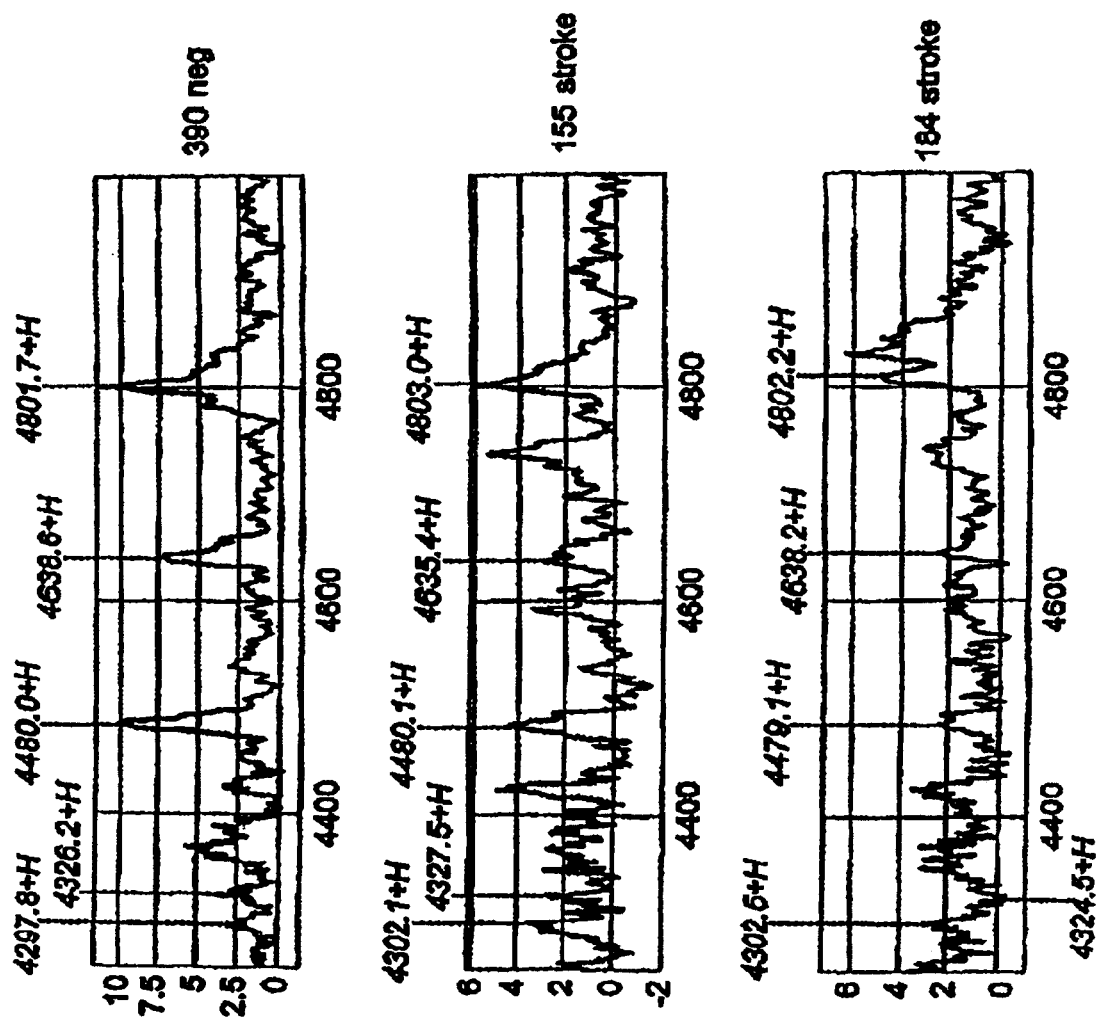
Figure 7C:
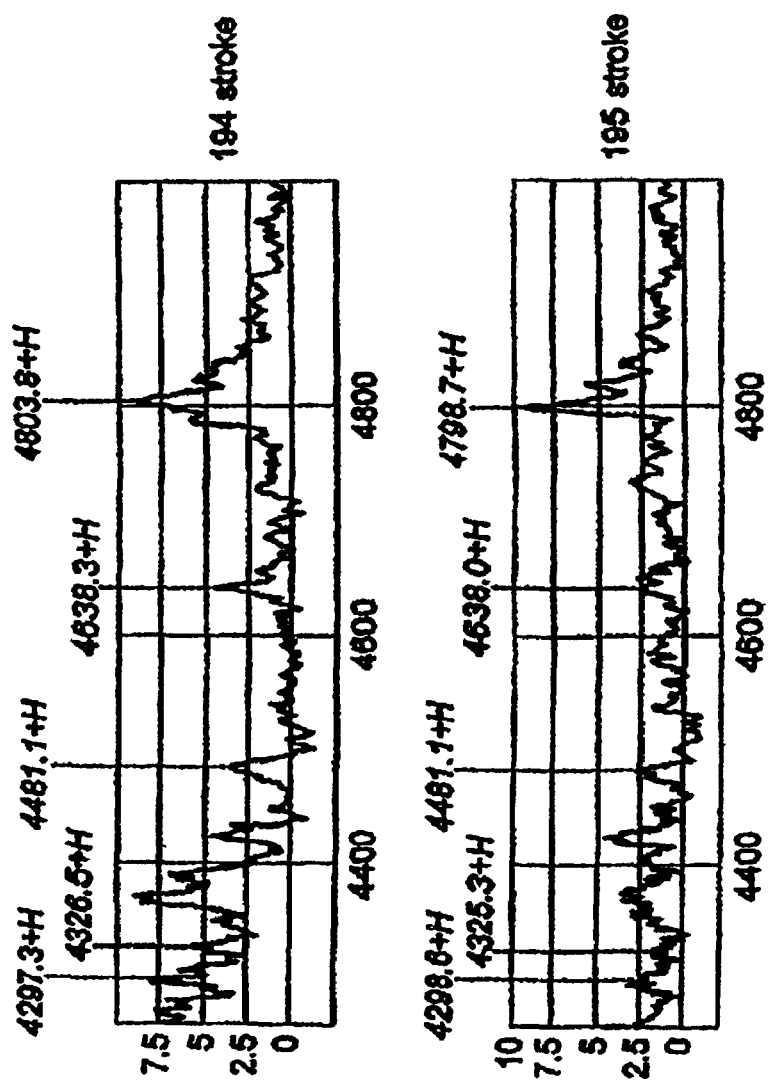
Figure 8A:
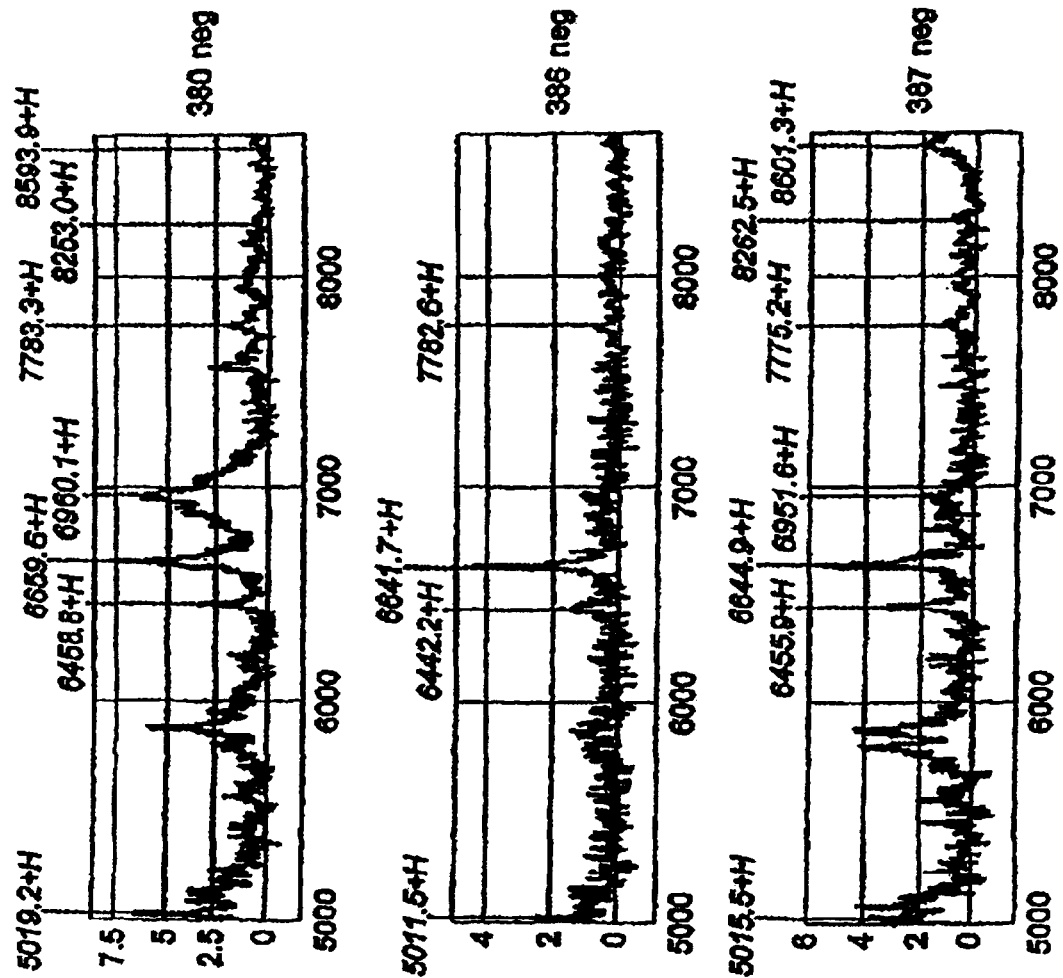
FIGS. 8 (A, B and C) is a view corresponding to FIG. 7, but in the molecular weight range of about 5000 to 8000 Da.
Figure 8B:
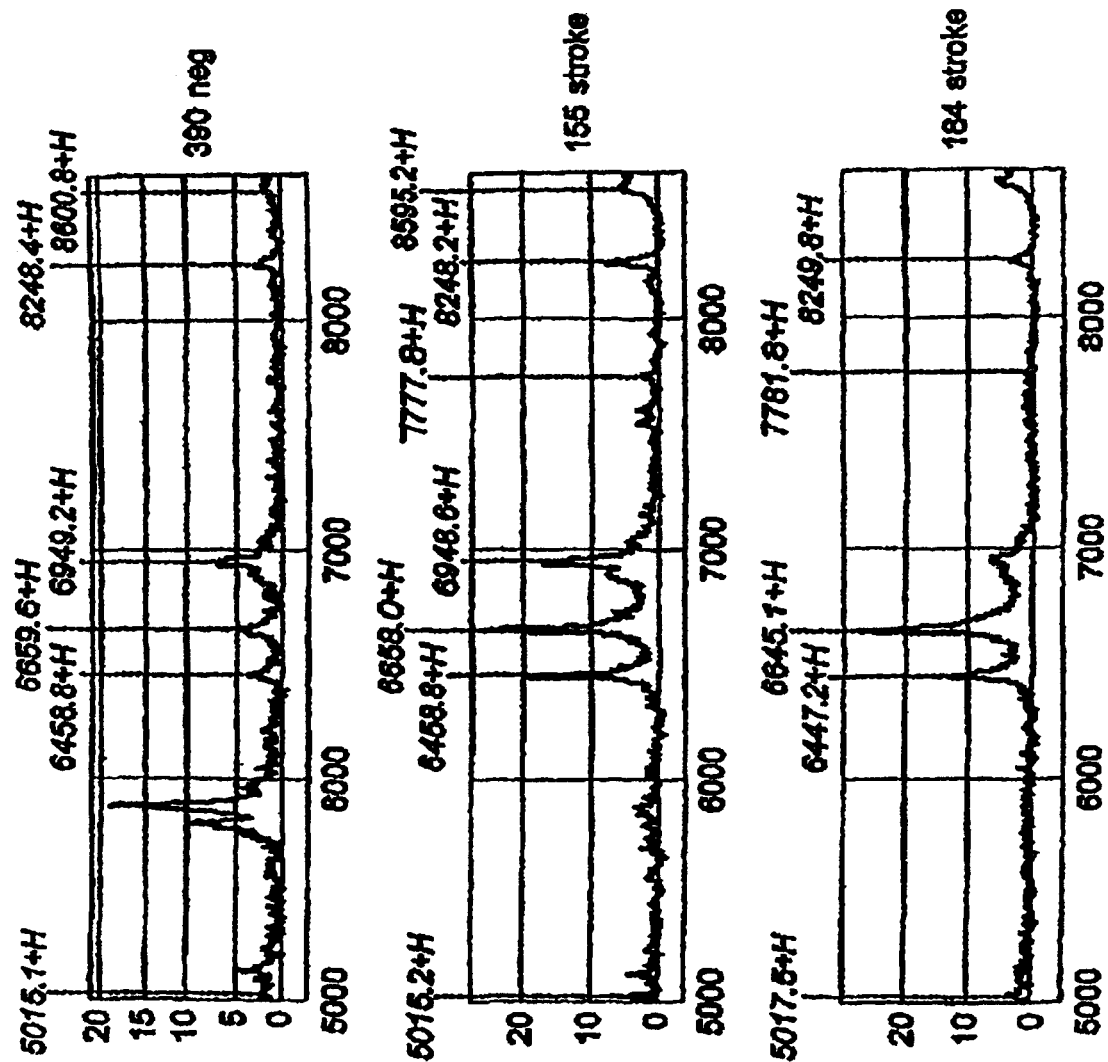
Figure 8C:
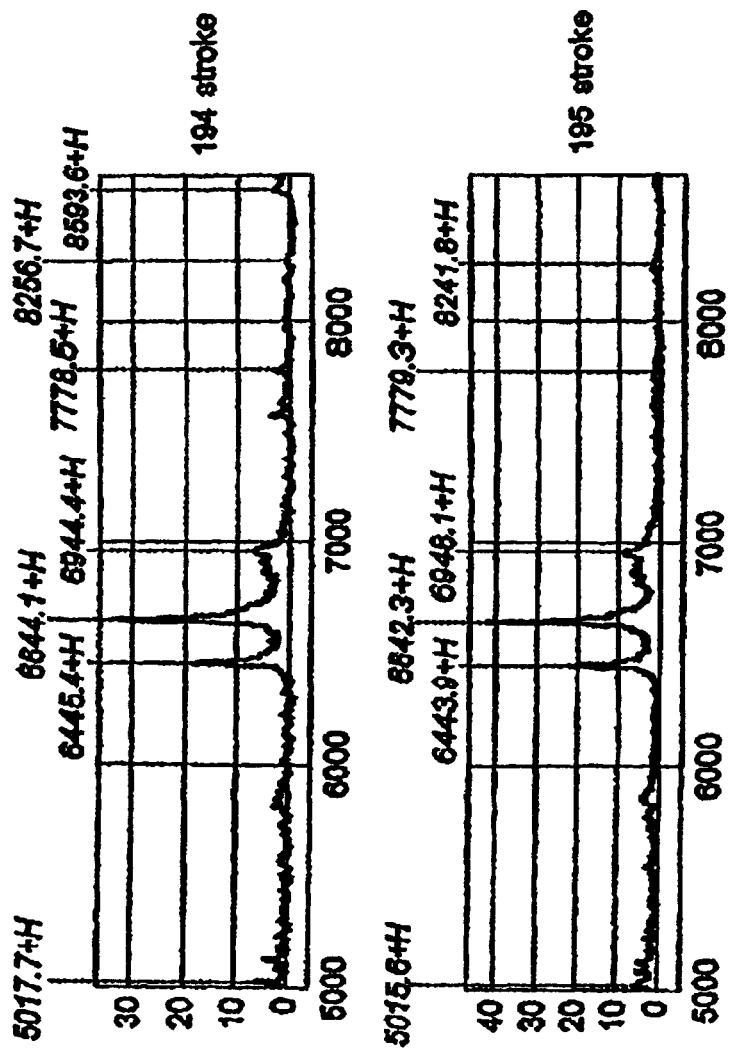
Figure 9A:
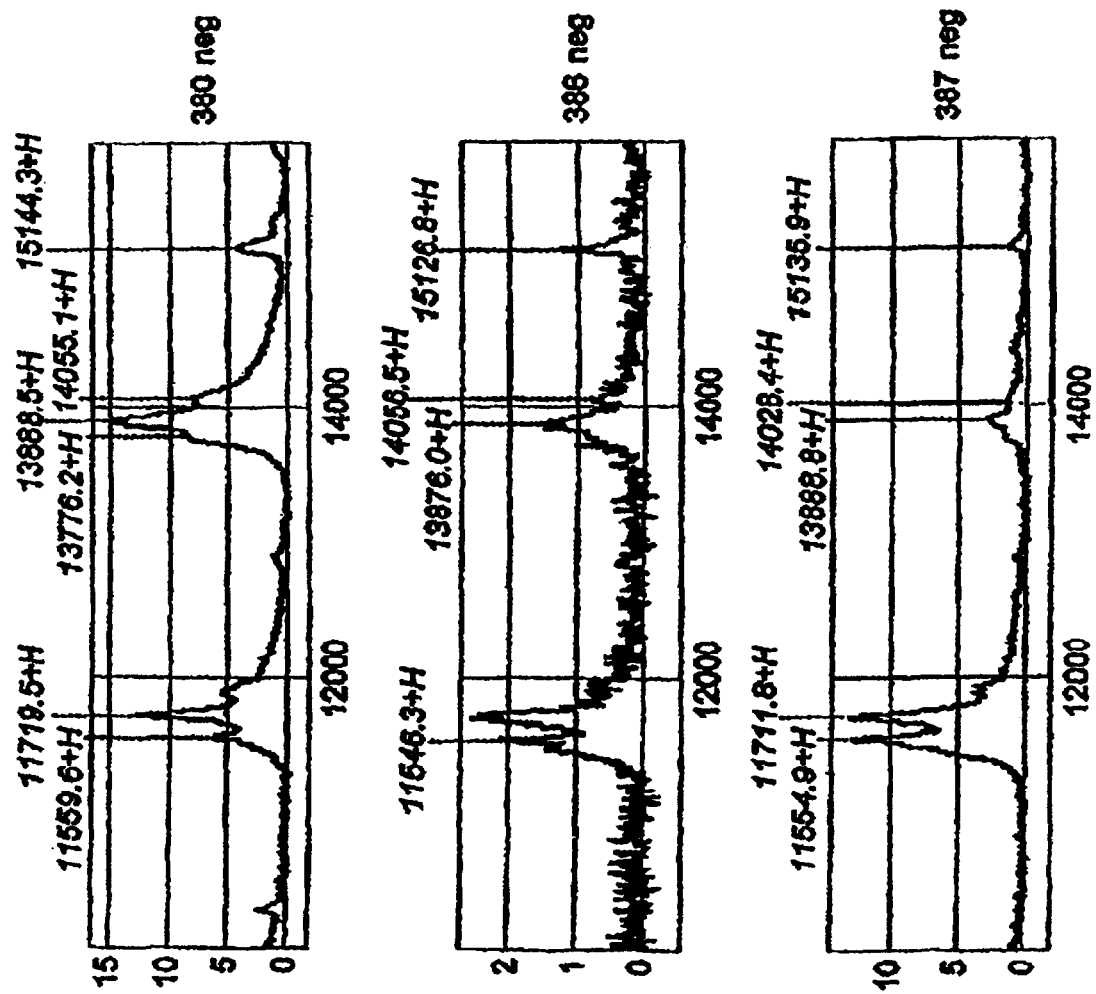
FIGS. 9 (A, B and C) is a view corresponding to FIG. 7, but in the molecular weight range of 10000 to 16000 Da.
Figure 9B:
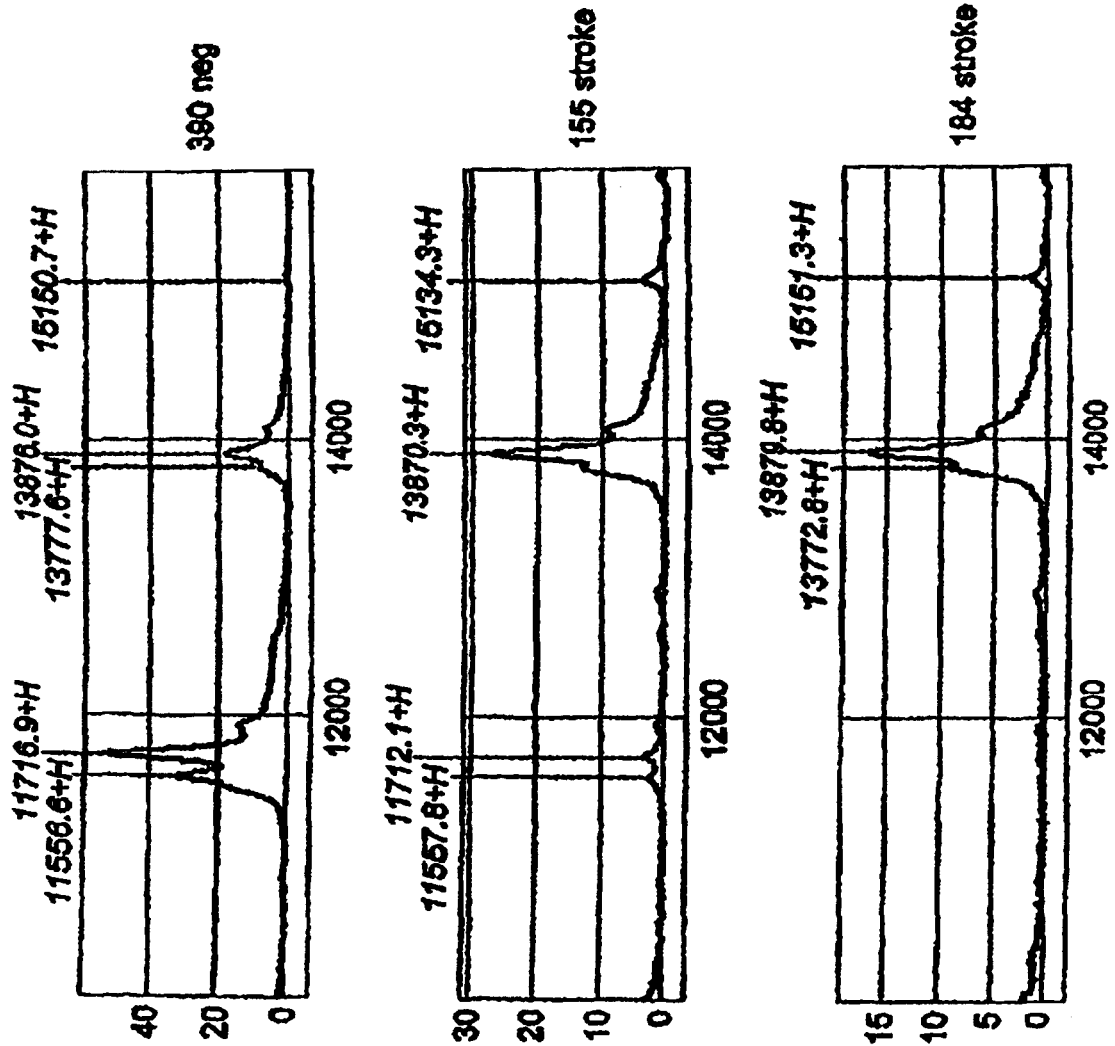
Figure 9C:
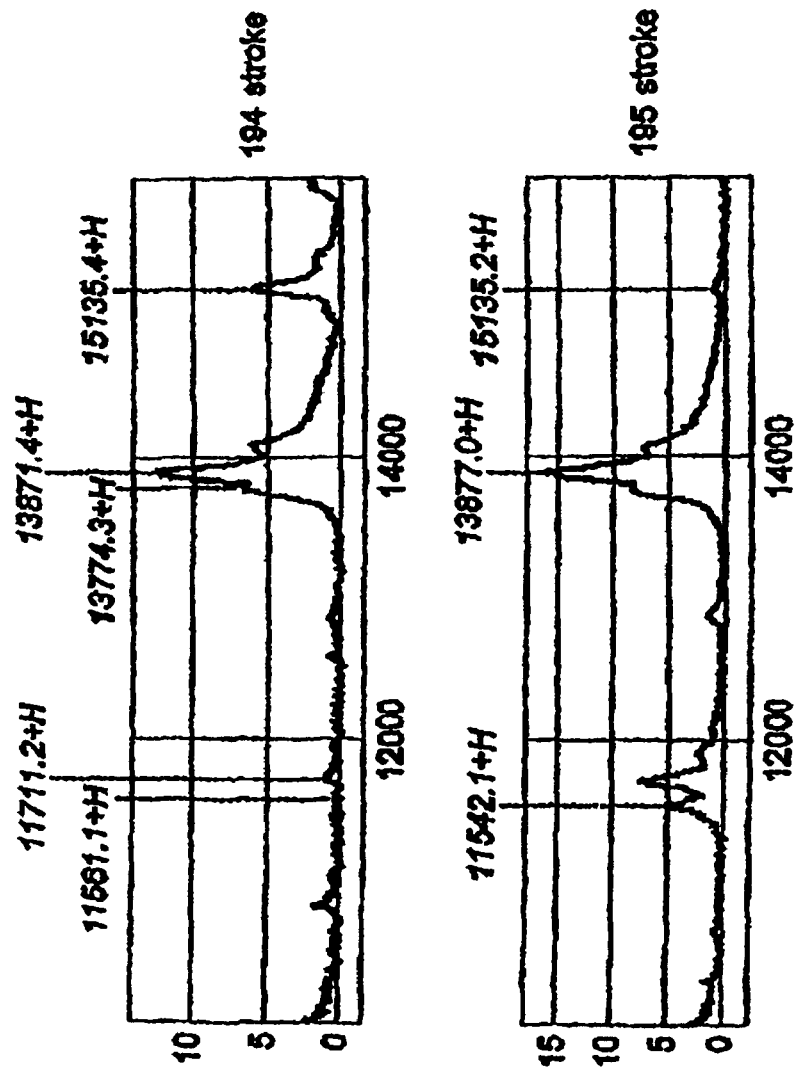

A comparative investigation between plasma samples coming from 21 stroke patients (including 10 haemorrhagic, 10 ischaemic and 1 unknown type) and 21 healthy patients was carried out using the SELDI technology, in a similar way to the procedure of Examples 1 and 2 except for the variations mentioned hereafter. SAX ProteinChips (Ciphergen) and a SPA (Ciphergen) matrix were retained for the study. An example of 4 stroke spectra and 4 healthy patient spectra among the 42 tested is given in FIGS. 7 to 9. Using the Biomarker Wizard (Mann and Whitney statistical analysis), seven peaks appeared differentially expressed between stroke and healthy controls: a decrease of the signal of the peaks at 4475 Da, 4634 Da and 4797 Da is indicative of stroke with p values of 0.000138, 0.00224 and 0.0132 respectively. An increase of the peaks at 6443 Da and 6641 Da is indicative of stroke with p values of 0.08950 and 0.02134. And a decrease of the peaks at 11530 Da and 11712 Da, relative to a control, is indicative of stroke with p values of 0.00634 and 0.04034 respectively.

Figure 11:
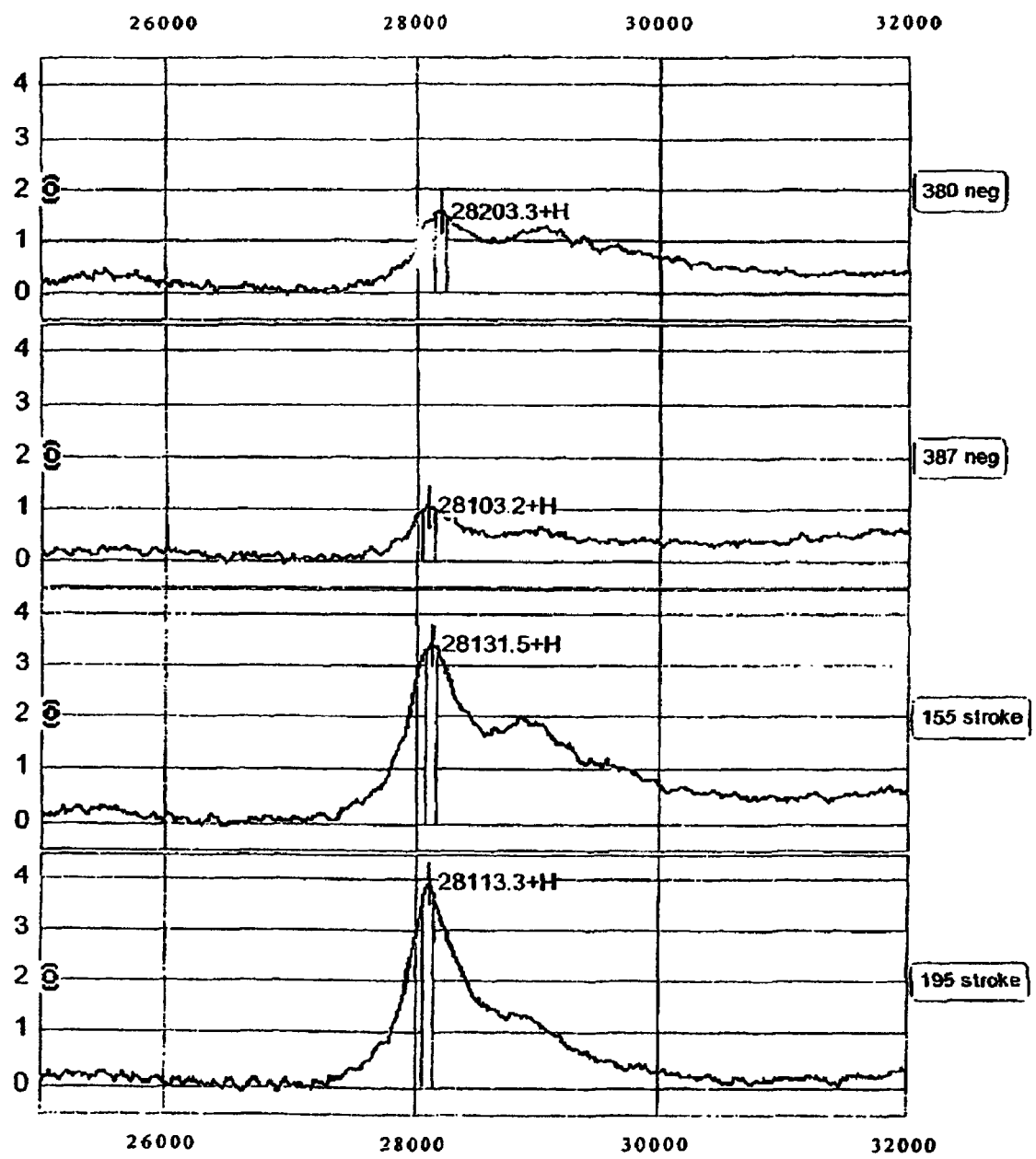
FIG. 11 is a spectral view of plasma from two stroke patients (identified as 155 stroke and 195 stroke) and two control samples (identified as 380 neg and 387 neg) using laser desorption/ionization mass spectrometry, in the molecular weight range of about 25000 to 32000 Da.

A further example of 2 stroke spectra and 2 healthy spectra is given in FIG. 11. A peak at around 28130 Da appeared differentially expressed between stroke and healthy controls: an increase of the signal of the peak at around 28130 Da is indicative of stroke.

The following protocol was used for the processing and analysis of the SAX ProteinChips:

1. Outline each spot using a hydrophobic pen. Allow to dry air
2. Apply 10 µl binding buffer (20 mM Tris-5 mM NaCl pH9.0) to each spot and incubate in a humidity chamber at room temperature for 5 minutes. Do not allow the spots to become dry.
3. Remove excess buffer from the spots without touching the active surface. Repeat steps 2 and 3 two more times.
4. Load 1 µl crude plasma sample+2 µl binding buffer (20 mM Tris-5 mM NaCl pH9.0)
5. Incubate in a humidity chamber for 30 minutes.
6. Wash each spot with 5 µl binding buffer (20 mM Tris-5 mM NaCl pH9.0) 5 times, followed by two quick washes with water (5 µl per wash).
7. Wipe dry around the spots. Apply 0.5 µl SPA saturated matrix (Ciphergen) to each spot while it is still moist, but not wet. Air dry. Apply a second 0.5 µl of SPA saturated matrix (Ciphergen) and air dry again before analysis of the retained protein on each spot with laser desorption/ionization time-of-flight mass spectrometry
8. The protein chip array was inserted into the instrument and analysed once the appropriate detector sensitivity and laser energy have been established to automate the data collection.

Example 4

SELDI Chips Stripping and Mono-Dimensional Electrophoresis

SAX SELDI chips were loaded with either negative control or stroke plasma samples (8 wells each) and stripped using the Laemmli buffer. The stripped proteins were loaded on a 1-DE SDS-PAGE gel as described below.

Tris-Glycine Gels: 10 µl of the above stripped samples were mixed with 10 µl of denaturing Laemmli buffer [1]. The samples were heated to 95° C. for 5 min, and loaded on a 15% T SDS-polyacrylamide gel according to the method of Laemmli. Gels were stained in a solution containing Coomassie Brilliant Blue R-250 (0.1% w/v) and methanol (50% v/v) for 30 min. Destaining was done in a solution containing methanol (40% v/v) and acetic acid (10% v/v).

Tris-Tricine Gels: Tris-tricine SDS-PAGE electrophoresis was performed according to Schagger and Von Jagow [2] using pre-cast 16.5% T gels (Bio-Rad, Hercules, Calif.). The anode buffer consisted of 0.2M Tris-HCl, pH 8.9 and the cathode buffer consisted of 0.1M Tris-HCl, 0.1M Tricine, 0.1% SDS, pH 8.25. 10 µl of each of the above stripped samples were mixed with 10 µl of 50 mM Tris-HCl, 4% (w/v) SDS, 12% (w/v) sucrose, 5% (v/v) β-mercaptoethanol, and a trace of bromophenol blue pH 6.8. After denaturation at 95° C. for 5 min, samples were loaded onto the gel. Gels were run at 80V for 3 hours. After electrophoresis, gels were fixed in 40% methanol, 10% acetic acid for 30 min. Gels were then stained with Colloidal coomassie blue G250 overnight and destained in 30% methanol. Bands to be identified were immediately cut, placed in an eppendorf tube and kept at 4° C. until further analysis. The apparent molecular masses were determined by running polypeptide molecular weight standards: Triosephosphate isomerase MW 26,625; Myoglobin MW 16,950; β-lactalbumin MW 14,437; Aprotinin MW 6,512; Insulin β chain, oxidized MW 3,496 and Bacitracin MW 1,423 (Bio-Rad).

Example 5

Protein Digestion and Peptide Extraction

Cores of gels containing proteins of interest were cut out for protein digestion with trypsin using previous published procedures [3] and modified as described below. The piece of gel was first destained with 100 µl of 50 mM ammonium bicarbonate, 30% (v/v) acetonitrile during 15 min at room temperature. Destaining solution was removed and replaced by 25 µl of 10 mM 1,4-Dithioerythritol in 50 mM ammonium bicarbonate and incubated 35 min at 56° C. 1,4-Dithioerythritol solution was then replaced by 25 µl of 55 mM iodoacetamide in 50 mM ammonium bicarbonate and incubated during 45 min at room temperature in the dark. Gel pieces were washed for 10 min with 100 µl of 50 mM ammonium bicarbonate and for 10 min with 100 µl of 50 mM ammonium bicarbonate and 30% (v/v) acetonitrile. Gel pieces were then dried for 30 min in a Hetovac vacuum centrifuge (HETO, Allerod, Denmark). Dried pieces of gel were rehydrated for 45 min at 4° C. in 5-20 µl of a solution of 50 mM ammonium bicarbonate containing trypsin at 6.25 ng/µl. After overnight incubation at 37° C., gel pieces were dried under high vacuum centrifuge before being rehydrated by the addition of 20 µl of distilled water and finally dried again in a speed-vac for 30 min. Extraction of the peptides was performed with 20 µl of 0.1% (v/v) trifluoroacetic acid (TFA) for 20 min at room temperature with occasional shaking. The TFA solution containing the peptides was transferred to a polypropylene tube. A second elution was performed with 20 µl of 0.1% (v/v) TFA in 50% (v/v) acetonitrile for 20 min at room temperature with occasional shaking. The second TFA solution was pooled with the first one. The volume of the pooled extracts was reduced to 1-2 µl by evaporation under vacuum. Control extractions (blank cores) were performed using pieces of gels devoid of stained proteins.

Example 6

Protein Identification by Peptide Mass Fingerprinting Analysis 1.5 µl of sample was placed on a MALDI 100-well target plate. Identical volumes of matrix (10 mg/ml □-Cyano-4-hydroxycinnamic acid in 50% (v/v) acetonitrile, 0.1% (v/v) TFA) were added to the previously loaded digest. Samples were dried as quickly as possible using a vacuum container. Mass measurement from liquid solution were conducted with a MALDI-TOF mass spectrometer Voyager™ Elite and super STR (Applied Biosystems, Framingham, Mass., USA) equipped with a 337 nm nitrogen laser. The analyser was used in the reflectron mode at an accelerating voltage of 20 kV, a delayed extraction parameter of 100-140 ns and a low-mass gate of 850 Da. Laser power was set slightly above threshold (10-15% higher than the threshold) for molecular ion production. Spectra were obtained by summation of 10 to 256 consecutive laser shots. Masses of the 60 highest peaks were extracted from the spectra and used for protein identification using the SmartIdent peptide mass fingerprint tool [4]. The research was conducted with SWISS-PROT and TrEMBL databases. The query was restricted to human proteins, the minimum number of matched masses was 4, the maximal tolerance for masses was 50 ppm after an internal calibration using autolysis product of trypsin, at most one missed cleavage for tryptic peptides was allowed, and the modifications accepted were carboxymethylation with iodoacetamide of cysteines and artifactual oxidation of methionines.

Example 7

Protein Identification by Peptide Fragmentation Analysis (Q-TOF and MALDI-TOF/TOF)

Q-TOF: Prior to nanoLC separation, the volumes of peptide containing solutions were adjusted to 7 µl by addition of a 0.1% (v/v) formic acid solution. Samples were settled in a Triathlon autosampler (Spack, Emmen, Holland). For each experiment, 5 µl of peptide containing solution were injected on a C18 reverse phase column of 75 µm inner diameter (YMS-ODS-AQ200, Michrom Bioresource, Auburn, Calif.). Peptides were eluted with an acetonitrile gradient in the presence of 0.1% (v/v) formic acid, using SunF low pumps (SunChrom, Friderichsdorf, Germany). A flow splitter was used in order to decrease the flow rate after the pumps from 200 to 0.4 µl/min. Peptides were analysed with a Q-TOF mass spectrometer (Micromass, Wythenshawe, England). A 2700V tension was applied on the nano-electrospray capillary (New Objective, Woburn, Mass., USA). Argon was used as collision gas. The collision energy was settled as a function of the precursor ion mass. MS/MS spectra were acquired by automatic switching between MS and MS/MS mode. Acquired MS/MS data were converted in a compatible format (DTA files) by ProteinLynx software (Micromass, Wythenshawe, England) and analysed using MASCOT search engine with SWISS-PROT, TrEMBL, NCBInr and EST databases. In cases of manual interpretation of MS/MS data, identification was performed by sequence only search using Protein-Info search engine from PROWL.

MALDI-TOF/TOF: MS and MS/MS analyses were also performed on the Applied Biosystems Voyager TOF/TOF™

Workstation, which uses a 200 Hz Nd:YAG laser operating at 355 nm. During MS/MS analysis, air was used as the collision gas. Spectra were obtained by accumulation of 200 to 2000 consecutive laser shots. Peak harvesting was done automatically using Data Explorer software. Peak resolution was calculated using the Data Explorer software, with only baseline correction being applied to the raw data. The query was made for the bovine species with a minimum number of matched masses set as 4. The maximum tolerance for masses was 50 ppm after an internal calibration using autolysis products of trypsin, at most one missed cleavage for tryptic peptides was allowed, and the modifications accepted were carbamidomethyl cysteines and artifactual oxidation of methionines. SWISS-PROT & TrEMBL databases were used for the search. MS/MS interrogations were carried out, with the same parameters as previously described for the PMF research, using MS-TAG or MS-Pattern tools depending on the type of interrogation. Precursor peak error was set as 50-100 ppm and fragment tolerance was defined as 500-1500 ppm. No internal calibration of the MS/MS data was completed.

Example 8

Turbidimetric ApoC-III Immunoassay Detection

Using the CODAS MIRA plus automate, ApoC-III quantitation was performed (Apo C-III Auto N-Daiichi kit (Instruchemie)). 30 control and 29 stroke plasma samples (including 14 haemorrhagic, 13 ischemic and 2 unknown) were tested. The results are shown in FIG. 10. The statistical student t-test did not discriminate stroke vs. controls plasma samples. However, comparing ApoC-III amount in the 14 haemorrhagic and the 13 ischemic, the p value of 0.0342 indicated a significant differential expression of ApoC-III between populations. Above 6.5 mg/dL (cut off value), it is possible to diagnose an ischemic stroke with a sensitivity of 92.3% and a specificity of 71.4%.

Example 9

Immunonephelometric SAA Detection

In order to perform a quantitative analysis of SAA plasmatic levels stroke and control samples, an immunonephelometric kit (N Latex SAA, Dade Behring) was used. The test was run on an IMMAGE® Immunochemistry system. The analysis was performed on 25 stroke plasma and 25 healthy control samples. The SAA plasmatic level is globally higher in the control population (mean value=32.66 mg/L) relative to the stroke population (mean value=21.79 mg/L).

REFERENCES

[1] Laemmli, U. K., Nature 1970, 227, 680-5.
[2] Schagger, H. and Von Jagow, G., Anal. Biochem. 1987, 166, 368-79.
[3] Bienvenut, W. V., Sanchez, J. C., Karmime, A., Rouge, V., Rose, K., et al., Anal. Chem. 1999, 71, 4800-7.
[4] Gras, R., Muller, M., Gasteiger, E., Gay, S., Binz, P. A., et al., Electrophoresis 1999, 20, 3535-50.

Each of the above cited publications is herein incorporated by reference to the extent to which it is relied on herein.

The invention claimed is:

1. A method of diagnosis of stroke or the possibility thereof in a subject suspected of suffering from stroke, which comprises determining the concentration of at least one polypeptide selected from apolipoprotein (Apo) C-III, Serum Amyloid A, Apo C-I, Antithrombin III fragment and Apo A-I in a sample of body fluid obtained from the subject wherein the polypeptide is differentially contained in the body fluid of stroke-affected subjects and non-stroke-affected subjects, and the method includes determining whether the concentration of polypeptide in the sample is consistent with a diagnosis of stroke.

2. The method of claim 1, wherein an antibody to the polypeptide is used in determining of the concentration of the polypeptide.

3. The method of claim 1, wherein the body fluid is cerebrospinal fluid, plasma, serum, blood, tears or urine.

4. The method of claim 1, wherein the determination of the concentration of the polypeptide is used to determine whether a diagnosed stroke is of the ischemic or hemorrhagic type.

5. The method of claim 1, further comprising subjecting a sample of body fluid obtained from the subject to mass spectrometry to determine a test amount of the polypeptide in the sample, wherein the polypeptide is differentially contained in the body fluid of stroke-affected subjects and non-stroke-affected subjects; and determining whether the test amount is consistent with a diagnosis of stroke.

6. The method of claim 1, wherein the polypeptide is present in the body fluid of stroke-affected subjects and not present in the body fluid of non-stroke-affected subjects, whereby the presence of the polypeptide in a body fluid sample is indicative of stroke.

7. The method of claim 1, wherein the polypeptide is not present in the body fluid of stroke-affected subjects and present in the body fluid of non-stroke-affected subjects, whereby the non-presence of the polypeptide in a body fluid sample is indicative of stroke.

8. The method of claim 5, wherein the mass spectrometry is laser desorption/ionization mass spectrometry.

9. The method of claim 5, wherein the sample is adsorbed on a probe having an immobilized metal affinity capture (IMAC), hydrophobic, strong anionic or weak cationic exchange surface capable of binding the polypeptide.

10. The method of claim 5, wherein the polypeptide is determined by surface-enhanced laser desorption/ionization (SELDI) and time of flight mass spectrometry (TOF-MS).

11. The method of claim 1, wherein a plurality of peptides is determined in the sample.

* * * * *